United States Patent [19]
Shaffer et al.

[11] Patent Number: 5,590,651
[45] Date of Patent: Jan. 7, 1997

[54] BREATHABLE LIQUID ELIMINATION ANALYSIS

[75] Inventors: Thomas H. Shaffer, Lansdowne; Marla R. Wolfson, Philadelphia; Thomas F. Miller, Philadelphia; Raymond Foust, III, Philadelphia, all of Pa.

[73] Assignee: Temple University - Of The Commonwealth System of Higher Education, Philadelphia, Pa.

[21] Appl. No.: 373,662

[22] Filed: Jan. 17, 1995

[51] Int. Cl.$^6$ .......................... A61B 5/097; A61M 16/00
[52] U.S. Cl. .......................... 128/632; 128/716; 128/719; 128/200.14; 128/203.12; 128/204.18; 128/913
[58] Field of Search .................... 128/632, 716, 128/719, 200.14, 203.12, 204.18, 913; 422/84

[56] References Cited

U.S. PATENT DOCUMENTS

| | | | |
|---|---|---|---|
| 3,682,166 | 8/1972 | Jacobs | 128/145.8 |
| 3,794,026 | 2/1974 | Jacobs | 128/145.8 |
| 3,895,630 | 7/1975 | Bachman | 128/2.07 |
| 3,901,230 | 8/1975 | Henkin | 128/205.17 |
| 3,983,864 | 10/1976 | Sielaff et al. | 128/2 G |

(List continued on next page.)

OTHER PUBLICATIONS

Perry's Chemical Engineers' Handbook, Sixth Edition, McGraw Hill Book Co., New York, 1984, pp. 3–247, 3–254, 3–255, 3–282 through 285, 22–48 and 22–49.

McGraw–Hill Encyclopedia of Science & Technology, 6th Edition, 1987, vol. 5, pp. 222–223.

Breuninger, H., Rubenstein, S.C., Wolfson, M. R., Shaffer, T. H. Effect of exchange transfusion with a red blood cell substitute on neonatal hemodynamics and organ blood flows. *J. Pediatr Surg.* 28 (2), 144–150, 1993.

(List continued on next page.)

Primary Examiner—Lee S. Cohen
Attorney, Agent, or Firm—Seidel, Gonda, Lavorgna & Monaco, P.C.

[57] ABSTRACT

The amount of breathable liquid eliminated from a mammal through volatilization in the lungs and/or through skin transpiration is detected by measuring the amount of saturation of the expiratory gas by vapors or the breathable liquid. Instantaneous saturation values are employed to gauge the amount of interaction in the lungs between the breathable liquid and respiratory gas flowing therein and to control selected feedback operations to maintain the maximum possible amount of interaction therebetween. The saturation level of expiratory gas is also employed to optimize operating parameters or a system for recovering the breathable liquid from the expiratory gas, directly from the patient, or from a gas or liquid ventilator. The saturation level or expiratory gas is also employed to perform functional residual capacity studies and to correct for errors in conventional functional residual capacity measurements performed while a patient undergoes partial liquid ventilation. When breathable liquid is employed as a blood substitute, the quantification or the loss of the breathable liquid from volatilization and transpiration helps to determine when to replenish the breathable liquid in the bloodstream. Vapors of one form of breathable liquid, perfluorocarbon, are employed to determine the functional residual capacity of a mammal's lung.

35 Claims, 23 Drawing Sheets

U.S. PATENT DOCUMENTS

| | | | |
|---|---|---|---|
| 4,230,126 | 10/1980 | Elings | 128/671 |
| 4,232,665 | 11/1980 | Vaseen | 128/200.24 |
| 4,233,842 | 11/1980 | Raemer et al. | 73/861.04 |
| 4,252,827 | 2/1981 | Yokoyama et al. | 424/366 |
| 4,378,797 | 4/1983 | Osterholm | 604/24 |
| 4,444,498 | 4/1984 | Heinemann | 356/246 |
| 4,451,251 | 5/1984 | Osterholm | 604/24 |
| 4,470,298 | 9/1984 | Jibelian | 73/23.1 |
| 4,490,351 | 12/1984 | Clark, Jr. | 424/5 |
| 4,493,692 | 1/1985 | Reed | 604/4 |
| 4,538,605 | 9/1985 | Gedeon et al. | 128/205.24 |
| 4,586,500 | 5/1986 | Glynn | 128/204.14 |
| 4,586,511 | 5/1986 | Clark, Jr. | 128/653 |
| 4,657,532 | 4/1987 | Osterholm | 604/24 |
| 4,661,092 | 4/1987 | Popovich et al. | 604/26 |
| 4,676,774 | 6/1987 | Semm et al. | 604/26 |
| 4,721,677 | 1/1988 | Clark, Jr. | 435/291 |
| 4,775,522 | 10/1988 | Clark, Jr. | 424/9 |
| 4,781,676 | 11/1988 | Schweighardt et al. | 604/21 |
| 4,795,423 | 1/1989 | Osterholm | 604/24 |
| 4,850,371 | 7/1989 | Broadhurst et al. | 128/719 |
| 4,865,836 | 9/1989 | Long, Jr. | 424/5 |
| 4,891,629 | 1/1990 | Gajjar, et al. | 340/632 |
| 4,919,895 | 4/1990 | Heldebrant et al. | 422/129 |
| 4,928,687 | 5/1990 | Lampotang et al. | 128/207.14 |
| 4,960,568 | 10/1990 | Matsumoto et al. | 422/83 |
| 4,963,130 | 10/1990 | Osterholm | 604/24 |
| 4,966,578 | 10/1990 | Baier et al. | 604/26 |
| 4,993,415 | 2/1991 | Long | 128/653 A |
| 4,994,158 | 2/1991 | Kiimalainen et al. | 204/153.1 |
| 5,038,792 | 8/1991 | Mault | 128/718 |
| 5,047,010 | 9/1991 | Ams et al. | 604/26 |
| 5,072,726 | 12/1991 | Mazloomdoost et al. | 128/200.14 |
| 5,072,737 | 12/1991 | Goulding | 128/718 |
| 5,080,645 | 1/1992 | Hanig | 604/4 |
| 5,084,011 | 1/1992 | Grady | 604/24 |
| 5,111,827 | 5/1992 | Rantala | 128/719 |
| 5,137,510 | 8/1992 | VanDeripe | 604/28 |
| 5,149,319 | 9/1992 | Unger | 604/22 |
| 5,149,321 | 9/1992 | Klatz et al. | 604/52 |
| 5,158,536 | 10/1992 | Sekins, et al. | 604/20 |
| 5,178,155 | 1/1993 | Mault | 128/718 |
| 5,200,430 | 4/1993 | Federman | 514/772 |
| 5,207,220 | 5/1993 | Long | 128/207.14 |
| 5,213,570 | 5/1993 | VanDeripe | 604/28 |
| 5,234,405 | 8/1993 | Klatz et al. | 604/24 |
| 5,244,924 | 9/1993 | Meinert | 514/759 |
| 5,277,176 | 1/1994 | Habashi et al. | 128/200.24 |
| 5,279,288 | 1/1994 | Christopher | 128/204.18 |
| 5,291,879 | 3/1994 | Babb et al. | 128/200.26 |
| 5,309,903 | 5/1994 | Long | 128/203.12 |
| 5,335,650 | 8/1994 | Shaffer et al. | 128/200.24 |
| 5,437,272 | 8/1995 | Fuhrman | 128/913 |

OTHER PUBLICATIONS

Thomas, S. R., Clark, L. C., Acerman, J. L. MR imaging of the lung using liquid perfluorocarbons. *J Comput Assist Tomogr* 10: 529–537, 1986.

Avery, M. E. & Mead, J. Surface properties in relation to atelectasis and hyaline membrane disease. *Am J Dis Child*; 97; 517–523, 1959.

Brumley, G. W., Chernick, V., Hodson, A. H., Normand, C., Fenner, A., Avery, M. E. Correlations of mechanical stability, morphology, pulmonary surfactant, and phospholipid content in the developing lamb lung. *J. Clin Invest*; 46(5); 863–873, 1987.

Collaboration European Multicenter Study Group. Surfactant replacement therapy for severe neonatal distress syndrome: an international randomized trial. *Pediatrics* 82: 683–691, 1988.

Jobe, A. H., Ikkegami, M. Surfactant for treatment of respiratory distress syndrome. *Am Rev Respir Dis* 136: 1256–1275, 1987.

Calderwood, H. W., Ruiz, B. C., Tham, M. K., Modell, J. H., Hood C. I. Residual levels and biochemical changes after ventilation with perfluorinated liquid. *J. Appl Physiol* 139: 603–607, 1975.

Curtis, S. E., Fuhrman, B. P., Howland, D. F. Airway and alveolar pressures during perfluorocarbon breathing in infant lambs. *J. Appl Physio* 68(6): 2322–2328, 1990.

Koen, P. A., Wolfson, M. R., Shaffer, T. H. Fluorocarbon ventilation: maximal expiratory flows and $CO_2$ elimination. *Pediatr Res* 24: 291–296, 1988.

Modell, J. H., Gollan, F., Giammona, S. T., Parker, D. Effect of fluorocarbon liquid on surface tension properties of pulmonary surfactant. *Chest* 57: 263–265, 1970.

Sargent, J. S., Seffl, R. J. Properties of perfluoronated liquid. *Fed Proc Fed Am Soc Exp Biol* 29: 1699–1703, 1970.

Schweiler, G. H., Robertson, B. Liquid ventilation in immature newborn rabbits. Biol Neonate 29: 343–353, 1976.

Shaffer, T. H., Tran, N., Bhutani, V. K., Sivieri, E. M. Cardiopulmonary function in very pre-term lambs during liquid ventilation. *Pediatr Res* 17: 680–684, 1983.

Shaffer, T. H., Lowe, C. A., Bhutani, V. K., Douglas, P. R. Liquid ventilation: effects on pulmonary function in distressed, meconium–stained lambs. *Pediatr Res* 18: 47–52, 1984.

Shaffer, T. H., A brief review: Liquid ventilation. *Undersea Biomed Res* 14: 169–179, 1987.

Wolfson, M. R., Tran, N., Bhutani, V. K., Shaffer, T. H. A new experimental approach for the study of cardiopulmonary physiology during early development. *J. Appl Physiol* 65: 1436–1443, 1988.

Holaday, D. A., Fiserova–Bergerova, V. J. H., Modell, H. W. Uptake, distribution, and excretion of fluorocarbon FX–80 during liquid breathing in the dog. *Anesthesiology* 37: 387–394, 1972.

Model, J., Tham, M. K., Modell, J. H., Calderwood, B. C. Ruiz. Distribution and retention of fluorocarbon in mice and dogs after injection or liquid ventilation. *Toxicol Appl Pharmacol* 26: 86–92, 1973.

Greenspan, J. S., Wolfson, M. R., Rubenstein, S. D., Shaffer, T. H. Liquid ventilation of human preterm neonates. *J of Ped* 117: 106–111, 1990.

Wolfson, M. R. Pulmonary administration of drug (PAD): a new approach for drug delivery using liquid ventilation. *Faseb Journal* 4(4): A1105, 1990.

Wolfson, M. R., Greenspan, J. S., Shaffer, T. H. Pulmonary administration of vasoactive drugs (PAD) by perfluorocarbon liquid ventilation. *Pediatr Res* 29(4): 336A, 1991.

Greenspan, J. S., Wolfson, M. R., Rubenstein, S. D., Shaffer, T. H. Liquid ventilation of human preterm neonates. *J of Ped* 117: 106–111, 1990.

Wolfson, M. R. Pulmonary administration of drug (PAD): a new approach for drug delivery using liquid ventilation. *Faseb Journal* 4(4): A1105, 1990 (Abstract 1989).

Wolfson, M. R., Greenspan, J. S., Shaffer, T. H. Pulmonary administration of vasoactive drugs (PAD) by perfluorocarbon liquid ventilation. *Pediatr Res* 29(4): 336A, 1991 (Abstract 1991).

Greenspan, J. S., Wolfson, M. R., Rubenstein, S. D., Shaffer, T. H. Liquid ventilation of human preterm neonates. *J of Ped* 117: 106–111, 1990 (Abstract 1991).

Wolfson, M. R. Pulmonary administration of drug (PAD): a new approach for drug delivery using liquid ventilation. *Faseb Journal* 4(4): A1105, 1990.

Wolfson, M. R., Greenspan, J. S., Shaffer, T. H. Pulmonary administration of vasoactive drugs (PAD) by perfluorocarbon liquid ventilation. *Pediatr Res* 29(4): 336A, 1991.

Zelinka, M. J., Wolfson, M. R., Calligaro, I., Rubenstein, S. D., Greenspan, J. S., Shaffer, T. H. Direct pulmonary administration of gentamicin during liquid ventilation of the lamb: comparison of lung and serum levels to IV administration *Pediatr Res 29(4) 290a, 1991 (Abstract 1991)*.

Moskowitz, G. D., Dubin, S. E., Shaffer T. Technical Report: Liquid breathing trials & animals studies with a demand regulated liquid breathing system. *J. Assoc Adv Med Instr.* 9(1) 28–33, 1975.

Shaffer, T. H. and Moskowitz, G. D. An electromechanical demand regulated liquid breathing system. *IEEE Transactions on biomedical engineering BME*22(5), 412–416, 1975.

Shaffer, T. H., Rubinstein D., Moskowitz, G. D., Delivoria–Papdopoulos. Gaseous exchange and acid–base balance in premature lambs during liquid ventilation since birth. *Pediatr Res* 10: 227–231, 1976.

Forman, D. L., Bhutani, V. K., Tran N., Shaffer, T. H. A new approach to induced hypothermia. *J Surg Res* 40: 36–42, 1986.

Curtis, S. E., Peck, J. T., Kelly, D. R. Partial liquid breathing with perflubron improves arterial oxygenation in acute canine lung injury. *J Appl Physiol* 75(6), 2696–2702, 1933.

Falciglia, H. S. Failure to prevent meconium aspiration syndrome. *Obstet Gynecol* 71: 349, 1988.

Moses, D., Holm, B., Spitale, P., Liu, M., Enhorning, G. Inhibition of pulmonary surfactant by meconium. *Am J Obstet Gynecol* 164: 477–481, 1991.

Foust, R., Kechner, N., Wolfson, M. R., Shaffer, T. H. Comparison between gas ventilation and liquid perfluorocarbon ventilation in acute meconium lung injury. *Faseb* 1993 (Abstract 1992).

Siva, Subramamian, K. N., Keszler, M., Hoy, G. ECMO for severe neonatal respiratory failure. *Contemp pediatr* 4: 118, 1987.

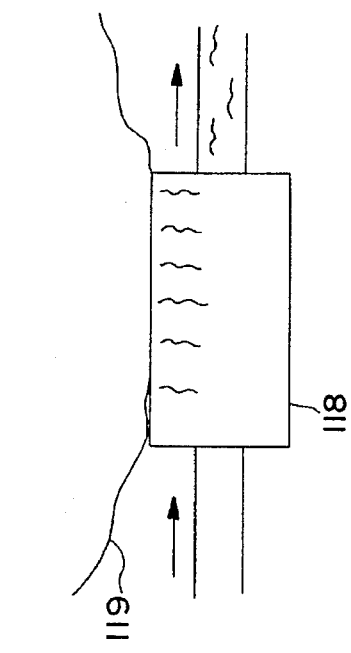
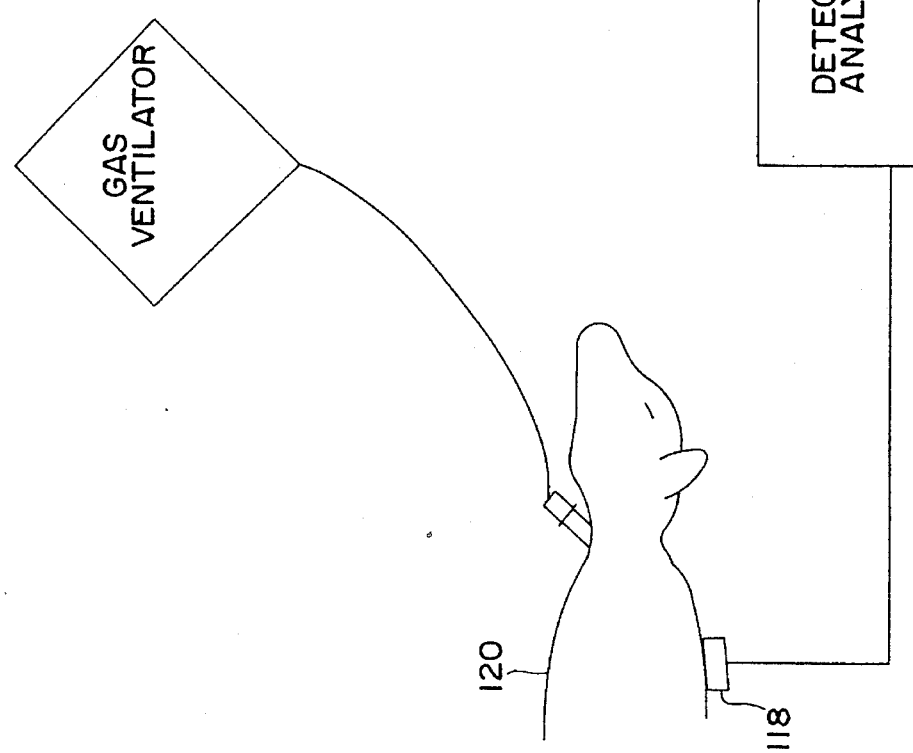
FIG.22B
FIG.22A

BREATHABLE LIQUID ELIMINATION ANALYSIS

FIELD OF THE INVENTION

This invention relates to methods and processes for determining and controlling the amount of interaction in a mammalian lung between a breathable liquid contained therein and respiratory gas in the lung. In addition, this invention relates to quantification of perfluorocarbon (PFC) volume loss from a system. This invention also relates to methods and processes for detecting breathable liquid vapors and employing measured values to detect and control breathable liquid recovery apparatus and other mammalian body functions. This invention also relates to methods and processes for detecting breathable liquid vapors and employing measured values to monitor the efficiency of an oxygen/carbon dioxide exchanger system.

BACKGROUND OF THE INVENTION

Mammalian respiration occurs by gas exchange through air sacs or alveoli in the lungs, and thus is referred to as "alveolar ventilation." FIG. 1 (prior art) shows pulmonary passageways which deliver and remove respiratory gases to and from the alveoli of lungs 200. In successive order, these passageways include the larynx 202, trachea 204, bronchus 206 and segmental bronchi or bronchioles 208. The bronchioles 208 terminate in small clusters of grapelike air sacs 210 (the alveoli) where the gas exchange occurs.

FIG. 2A (prior art) shows one alveolus 212 of the alveoli 210 and FIG. 2B (prior art) diagrammatically represents the gas exchange through the alveolus 212. A network of blood capillaries 214 covers or surrounds the alveolar walls 216. The gas-filled interior region of the alveolus 212 and the network of capillaries 214 are separated by less than 0.5 μm of intervening tissue. The gas exchange in alveolar lungs can be modeled as a ventilated pool 218, as shown in FIG. 2B.

During liquid ventilation, the pulmonary passageways of the lungs are filled with a breathable liquid which has the ability to deliver oxygen to, and remove carbon dioxide from, the pulmonary system. Two common types of liquid ventilation processes include "total liquid ventilation" and "partial liquid ventilation."

In a total liquid ventilation system, a breathable liquid is oxygenated and pumped or instilled into the lungs during an inspiratory breathing stage. When the breathable liquid reaches the alveoli, the oxygen in the breathable liquid diffuses into the blood of the capillaries surrounding individual alveolus. Correspondingly, carbon dioxide in the blood diffuses into the breathable liquid. The breathable liquid is then pumped out or removed from the lungs during an expiratory breathing stage. The expired liquid is scrubbed to remove the carbon dioxide, reoxygenated and returned to the lungs during a subsequent inspiratory breathing stage. A respirator typically performs the breathing stages. Such systems are described in U.S. Pat. Nos. 5,335,650 and 5,158,536, both of which are incorporated by reference herein in their entirety.

In a partial liquid ventilation system, a breathable liquid is instilled into the lungs and remains therein. This system is often employed when the lungs are collapsed since the volume of the breathable liquid functions to expand the lungs. The breathable liquid fills the alveoli. Then, respiratory gas is pumped into and out of the lungs. Oxygen carrying inspiratory respiratory gas interacts with the breathable liquid and releases the oxygen to the breathable liquid. In turn, the breathable liquid releases the oxygen into the blood surrounding the alveoli in the same manner as described above in the total liquid ventilation system. Likewise, carbon dioxide in the blood diffuses into the breathable liquid, which in turn, diffuses into areas of the lungs not taken up by the breathable liquid. During the expiratory phase, expiratory gas (including the carbon dioxide) exits the lung. As noted above, during partial liquid ventilation, the breathable liquid remains in the lungs, acting as an exchange medium for the oxygen and carbon dioxide entering and exiting the lungs. Partial liquid ventilation, as performed today, is not a closed loop system.

Breathable liquids employed today have various vapor pressures. During partial liquid ventilation, a small amount of the breathable liquid will volatilize or vaporize with each breathing cycle by saturating the respiratory gas. That is, the vapor pressure of the breathable liquid causes gas vapors coming off the liquid to saturate the respiratory gas as the gas flows through and around the liquid. During the expiratory phase, the saturated or partially saturated gas leaves the respiratory system. Since partial liquid ventilation is not a closed loop system, the volatilized breathable liquid must eventually be replaced by a new instillation of breathable liquid into the patient's lungs.

During partial liquid ventilation, a portion of the breathable liquid is also lost due to evaporation into the lungs. Some of this evaporated liquid becomes absorbed by the lungs and eventually leaves the patient's body by transpiration through the skin. Significant problems still exist in performing total and partial liquid ventilation. During total liquid ventilation, the breathable liquid also undergoes volatilization and dissolves in the expiratory liquid. Total liquid ventilation systems employed today scrub dissolved carbon dioxide from the expiratory liquid before the gas is reoxygenated and cycled back into the patient's lungs. This process occurs in an oxygenator/diffuser circuit. Not all of the carbon dioxide is scrubbed from the diffuser. Furthermore, none of the vaporized breathable liquid is recovered in the scrubber. Instead, it is vented to the environment. Accordingly, the system must periodically add more breathable liquid from a storage reservoir. This increases the cost of the liquid ventilation process since breathable liquid is expensive (e.g., as much as $2.00/ml).

During partial liquid ventilation, an operator must continually monitor the process to ensure that sufficient alveolar ventilation is occurring. One important aspect of the monitoring is to ensure that there is a sufficient quantity of breathable liquid in the lungs to promote the desired amount of alveolar ventilation. Alveolar ventilation can be compromised if the volume of liquid in the lung becomes too small.

Current techniques for measuring the amount of breathable liquid in the lungs are inaccurate and inadequate. One technique employed today involves merely replenishing the supply of breathable liquid in the lungs until they are filled. This is supposedly accomplished by visualizing a meniscus of PFC in the endotracheal tube. However, it is not always necessary or desirable to completely fill the lungs to achieve the desired amount of alveolar ventilation. Accordingly, the operator does not know for sure how much breathable liquid to add as volatilization depletes the store of liquid.

Oftentimes, the breathable liquid becomes maldistributed throughout the lungs due to patient movement or density differences which cause liquids to settle and gases to rise. For example, some bronchioles may have little or no breathable liquid to supply the alveoli at their distal ends, whereas other bronchioles may be overfilled. This maldistribution may also cause insufficient interaction between the breathable liquid and the respiratory gas. Atelectasis may also cause insufficient interaction between the breathable liquid and the respiratory gas. Atelectasis is the collapse of the expanded lung or the defective expansion of the pulmonary alveoli at birth. Currently, the operator of a liquid ventilation system has no sure technique for gauging whether insufficient alveolar ventilation is the result of an inadequate quantity of breathable liquid in the lungs, maldistribution of the breathable liquid or atelectasis.

Furthermore, the volatilized liquid in the expiratory gas is vented to the environment in the same manner as the total liquid ventilation system. Again, this loss of a valuable substance raises the cost of the overall process.

The inability to accurately detect the amount of breathable liquid in the patient's lungs complicates effective patient management.

Accordingly, there is still a need for apparatus and methods to improve liquid ventilation processes. Specifically, there is a need for apparatus and methods which allow the operator to more accurately gauge the amount and distribution of breathable liquid in a patient undergoing partial liquid ventilation, the amount being lost due to vaporization or through other evaporative channels and the amount of interaction between the breathable liquid and respiratory gases. There is also a need for apparatus and methods to scavenge or recover vaporized breathable liquid from expiratory gas and to monitor the efficiency of the recovery equipment. The current invention fills these needs.

DEFINITIONS

The terms "pulmonary pathways" and "pulmonary system" are used herein interchangeably and refer to areas of the body which are normally occupied by air during normal breathing cycles. Such areas include, without limitation, pulmonary channels, spaces or volumes in the trachea, left and right bronchi, bronchioles, and alveoli of the lungs.

The terms "breathing liquid" and "breathable liquid" are used herein interchangeably and refer to a liquid which has the ability to deliver oxygen into, and to remove carbon dioxide from, the pulmonary system of a patient. Examples of breathable liquids often employed in liquid ventilation procedures include, without limitation, saline, perfluorochemicals, and the like. One of the presently preferred breathing liquids are perfluorocarbon ("PFC") liquids because at or around normal human body temperatures, most types of PFC liquids are relatively inert, non-biotransformable, non-toxic and chemically and thermally stable. Moreover, these liquids are especially suited for use in liquid ventilation procedures due to their physiological characteristics such as: low surface tension (i.e., about 75% less than that of $H_2O$); high solubility for oxygen (i.e., about 16 times greater than that of saline); high solubility for carbon dioxide (i.e., about 3 times greater than that of saline); and, relative biological inertness.

In the broadest sense, the scope of the invention includes the use of an oxygenated liquid fluorochemical, of which a perfluorochemical, such as perfluorocarbon (PFC) is one such embodiment.

PFC-gas interaction, as described herein, refers to the amount of physical contact between respiratory gases and a liquid body of PFC (or other types of breathable liquids).

SUMMARY

Breathable liquids, such as PFC, volatilize in the mammalian lung during partial liquid ventilation and are eliminated from the lung through the respiratory process. Such liquids are also lost from the lung by evaporation, leaving the body through skin transpiration. The amount of PFC in expiratory gas is a good indicator of PFC-gas interaction. Interaction is at its best when the expiratory gas is fully saturated with PFC vapor.

In one embodiment of the invention, the saturation level of PFC in the expiratory gas is detected and compared to known values for different levels of saturation, thereby yielding an accurate indication of PFC-gas interaction. The saturation level is also employed to control selected feedback operations of a partial liquid ventilation system to maintain the maximum possible amount of PFC-gas interaction.

In another embodiment of the invention, the saturation level is employed to correct for errors in conventional functional residual capacity measurements performed while a patient undergoes partial liquid ventilation.

In yet another embodiment of the invention, the saturation level is employed to assist in weaning a patient from a partial liquid ventilation system.

In yet another embodiment of the invention, the saturation level is employed to monitor and control a breathable liquid vapor recovery system associated with a total or partial liquid ventilation system.

In yet another embodiment of the invention, the saturation level is employed to quantify the amount of breathable liquid in the bloodstream. This is useful for detecting transpiration loss during partial liquid ventilation and when breathable liquid is employed as a blood substitute.

In yet another embodiment of the invention, vapors of PFC are employed to determine the functional residual capacity of a mammal's lung.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 22A shows a set-up for quantifying PFC evaporative loss during partial liquid ventilation.

FIG. 22B shows an exploded view of a collection region in the FIG. 22A set-up.

DESCRIPTION OF THE INVENTION

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

The invention described herein employs PFC as the breathable liquid. Thus, the description below refers to PFC liquid and PFC vapor. As noted above, however, other types of breathable liquid are within the scope of the invention.

Figure 1:
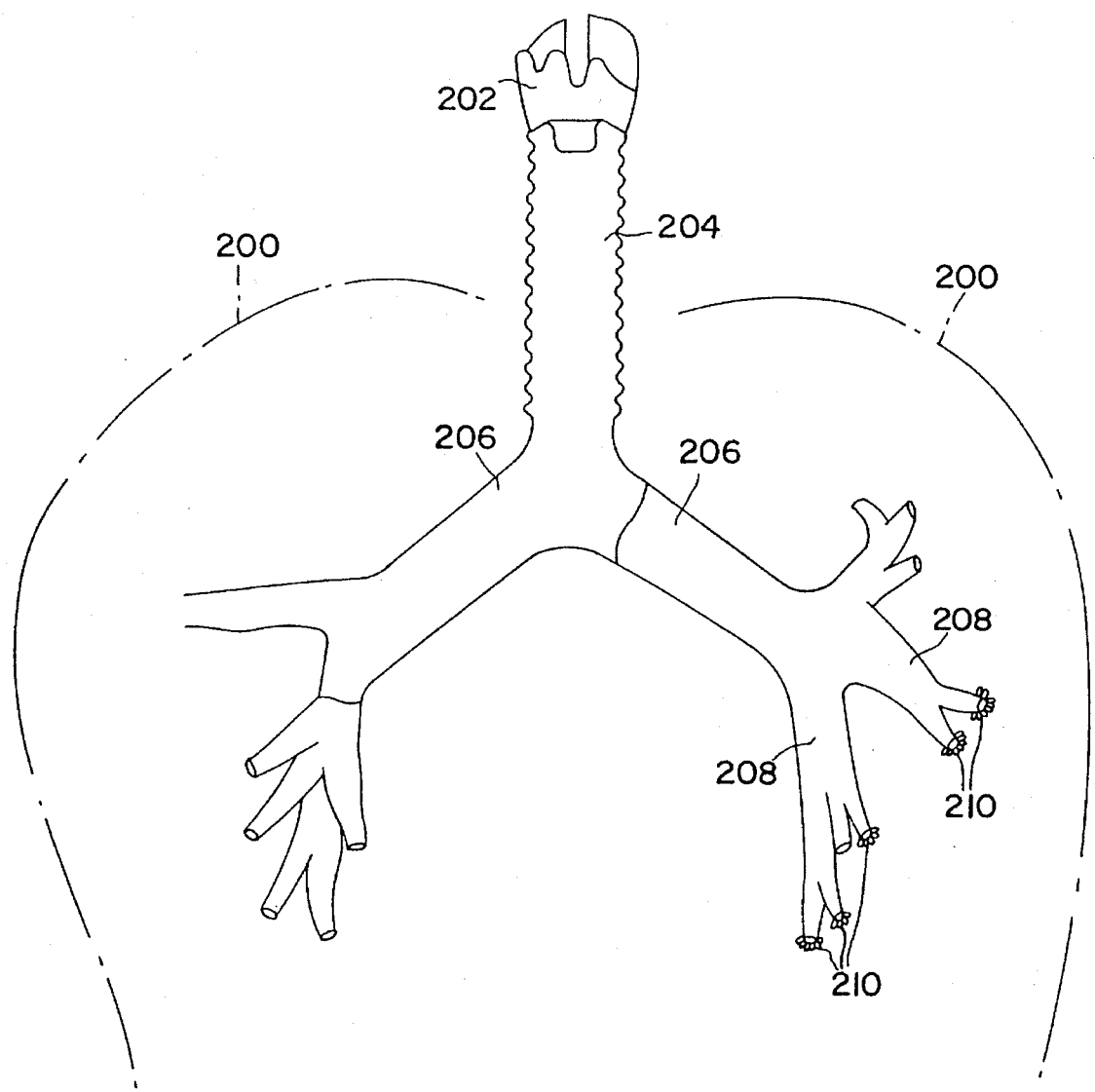
FIG. 1 is a prior art depiction of pulmonary passageways which deliver and remove respiratory gases to and from the alveoli.
Figure 2A:
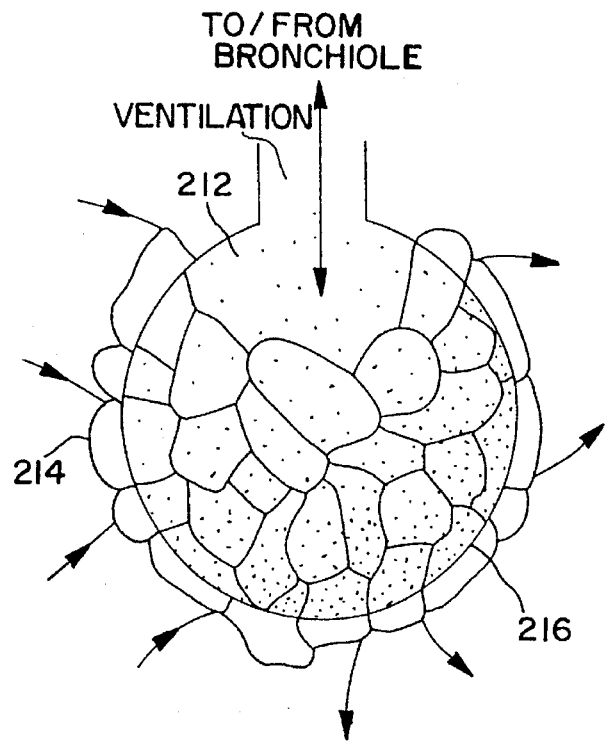
FIG. 2A is a prior art depiction of one alveolus of the alveoli.
Figure 2B:
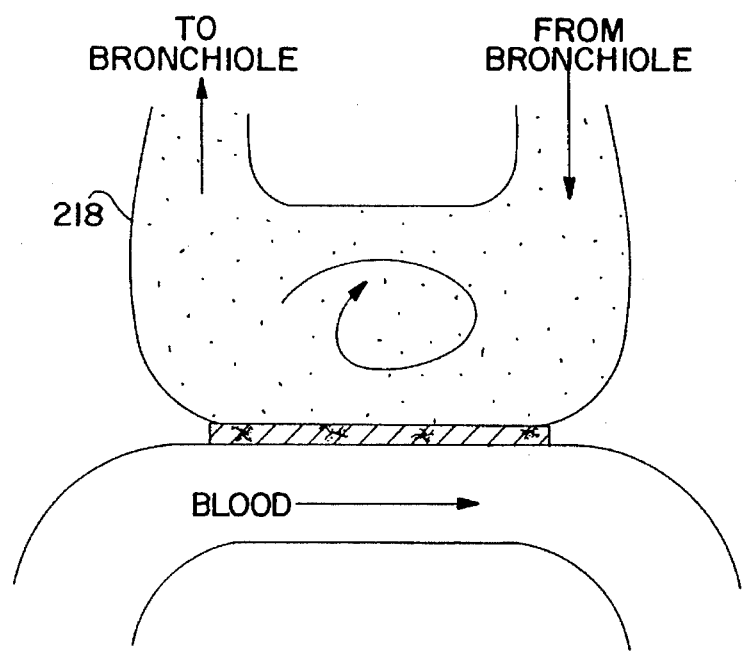
FIG. 2B is a prior art diagrammatical representation of the gas exchange through the alveolus of FIG. 2A.
Figure 3:
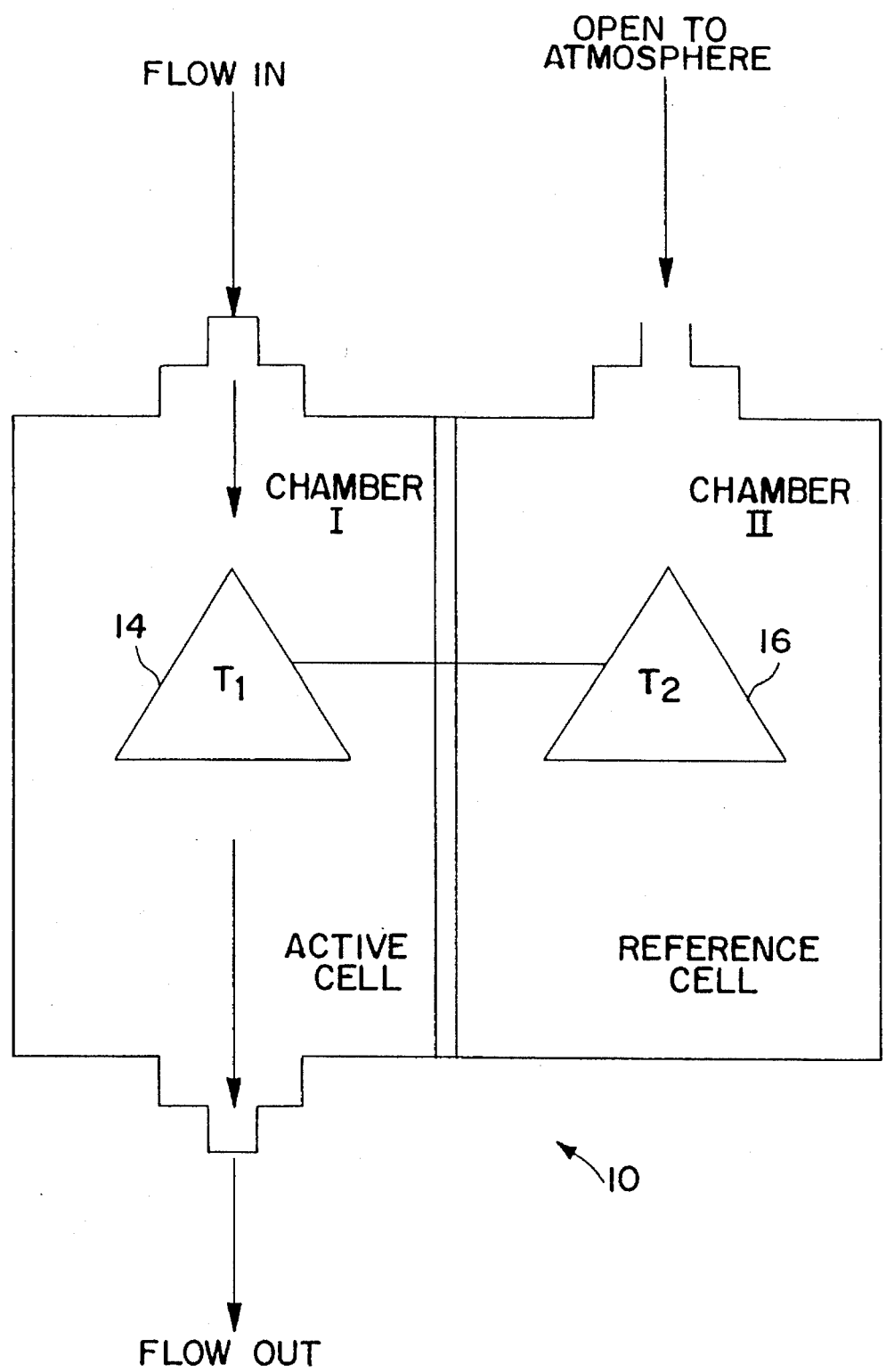
FIG. 3 is a schematic illustration of a preferred embodiment of a thermal conductivity detector apparatus of the invention.
Figure 4:
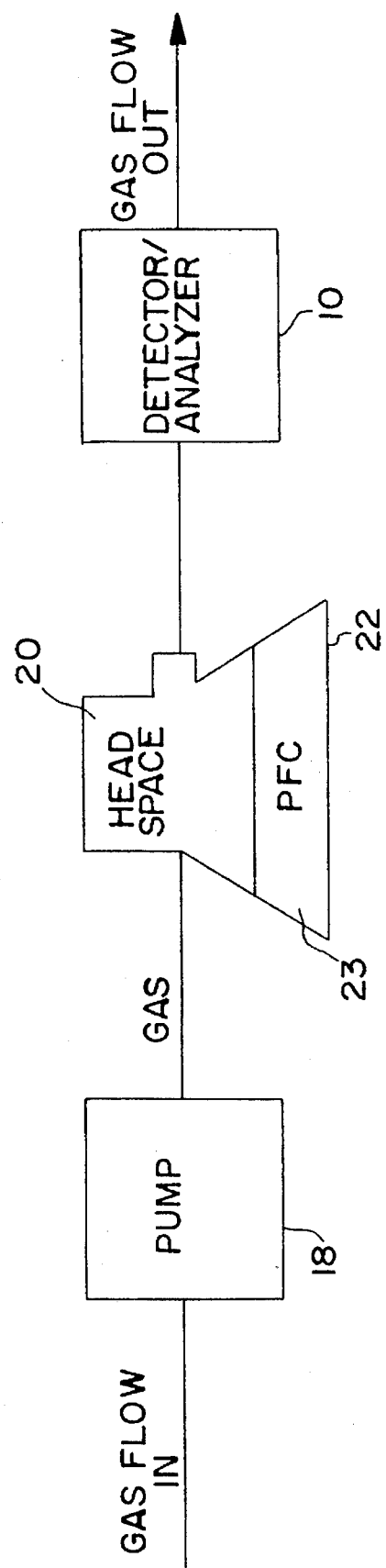
FIG. 4 is an in vitro schematic illustration of a set-up for measuring the thermal conductivity of gases using the detector in FIG. 3.
Figure 5:
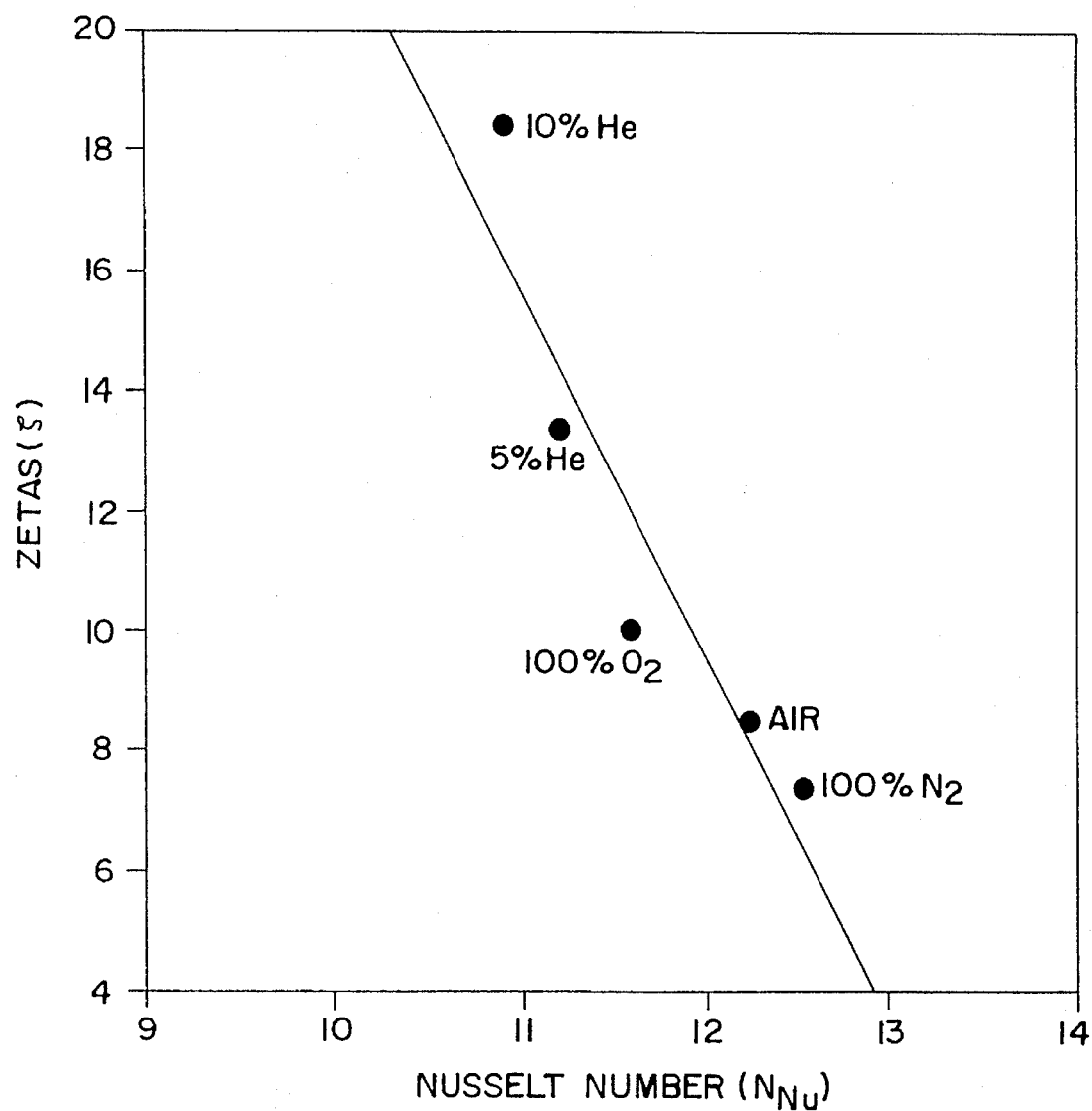
FIG. 5 graphically depicts the zeta value and Nusselt number for different carrier gases.
Figure 6:
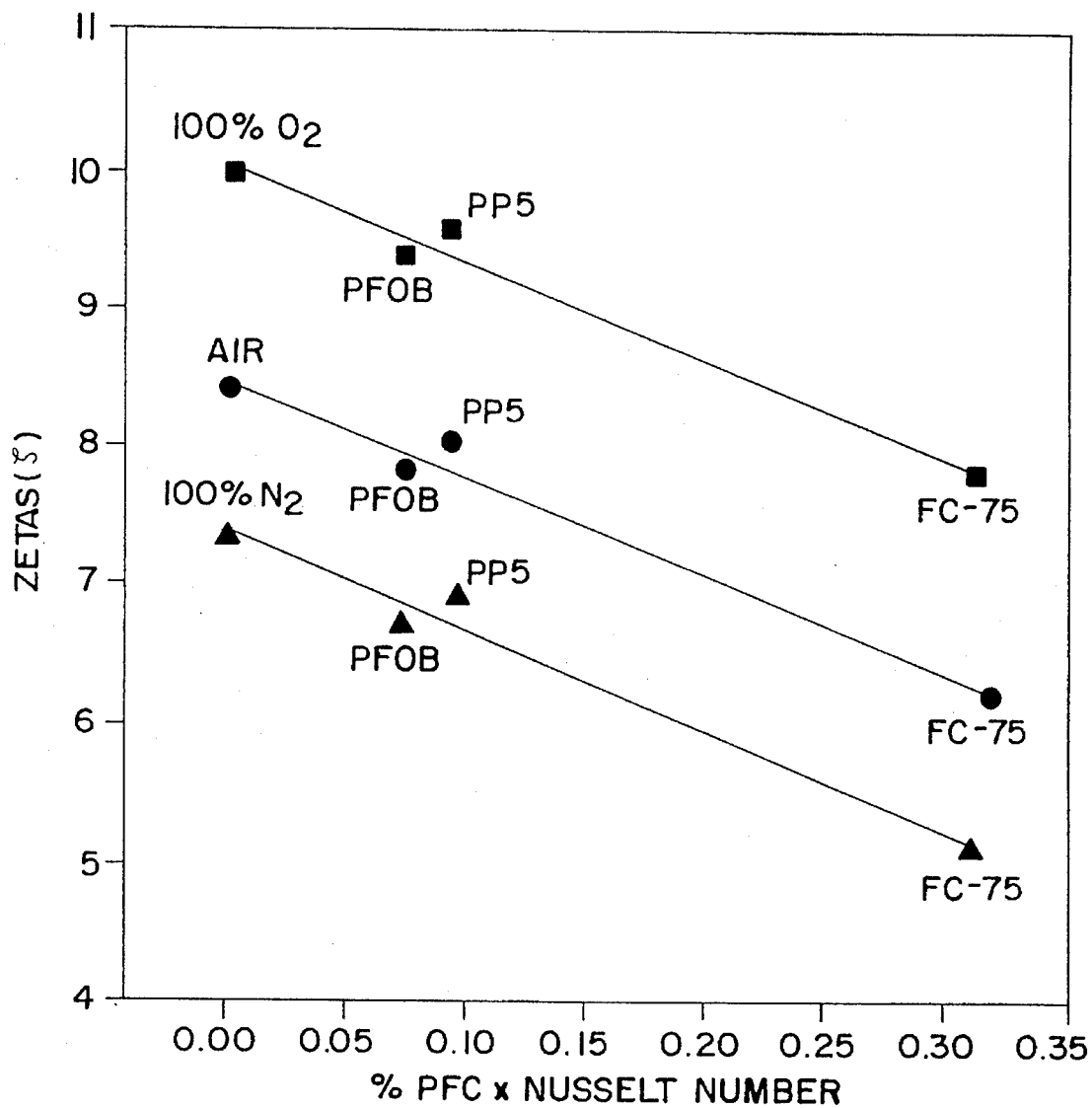
FIG. 6 graphically depicts the zeta value and % PFC multiplied by the Nusselt number for different carrier gases in their unsaturated state and when fully saturated by different PFC vapors.
Figure 7:
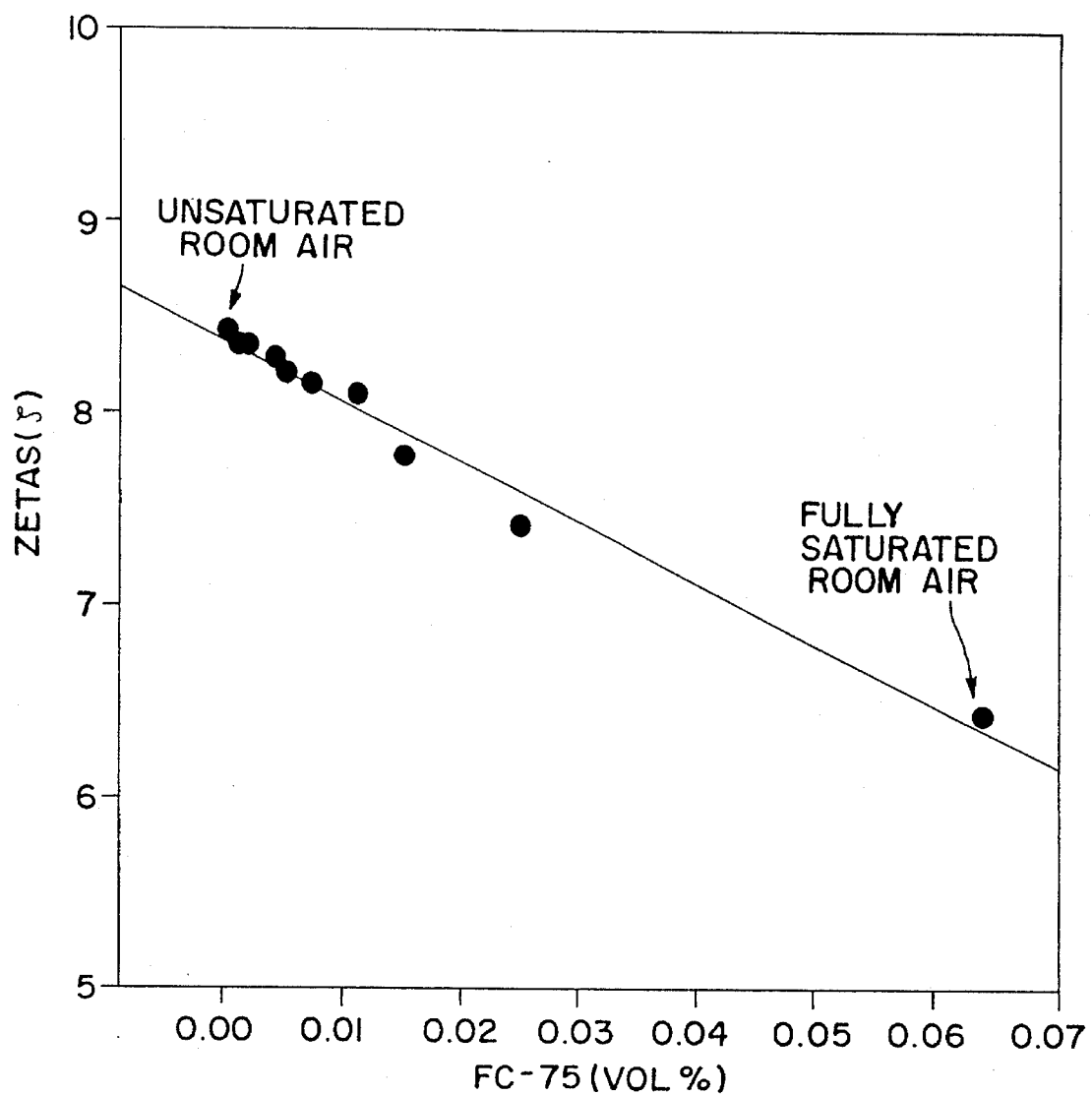
FIG. 7 graphically depicts zeta values for different volume dilutions of room air saturated with PFC vapor.
Figure 8:
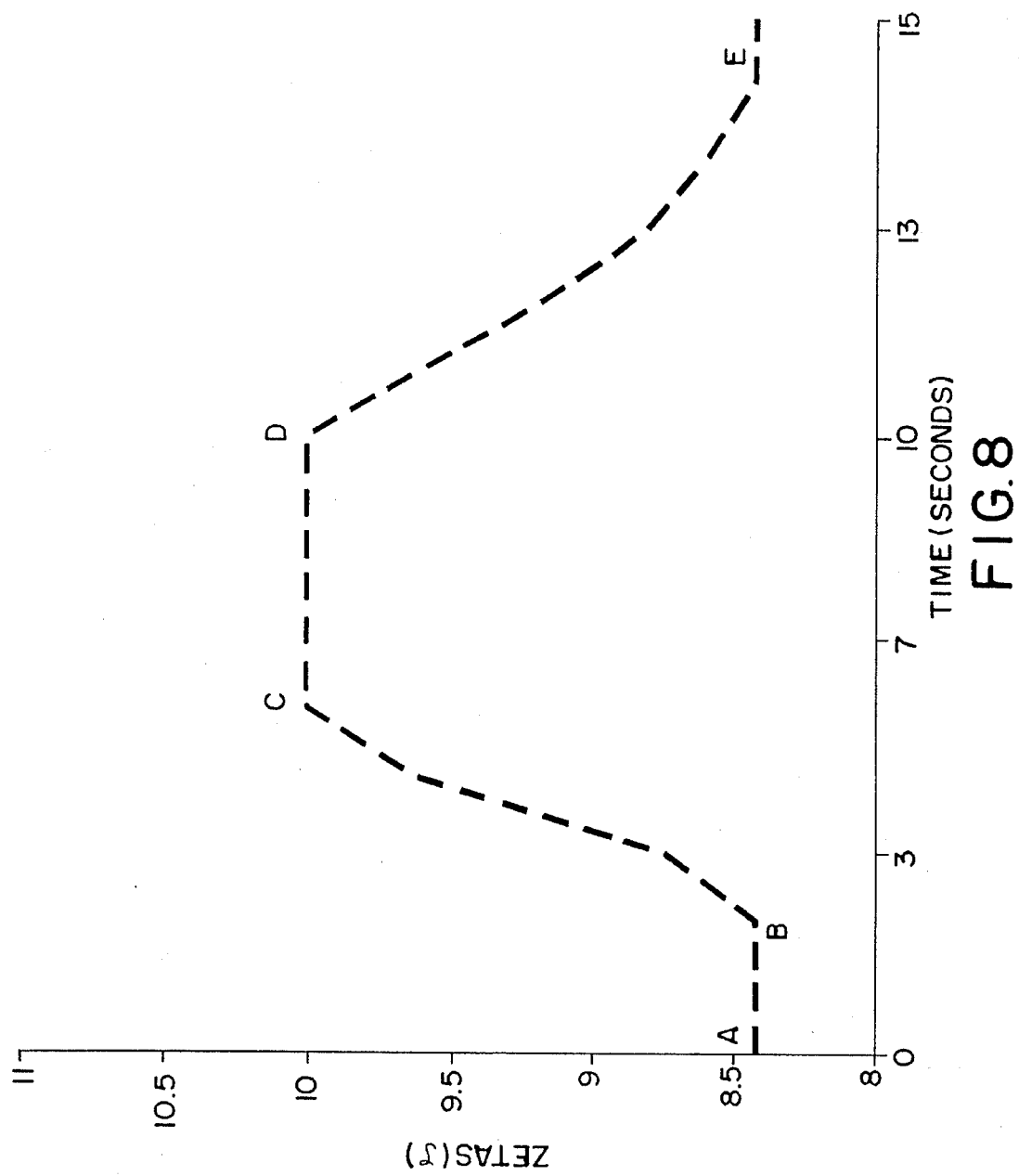
FIG. 8 graphically depicts calibration values for a measurement detector/analyzer suitable for use in the invention.
Figure 9:
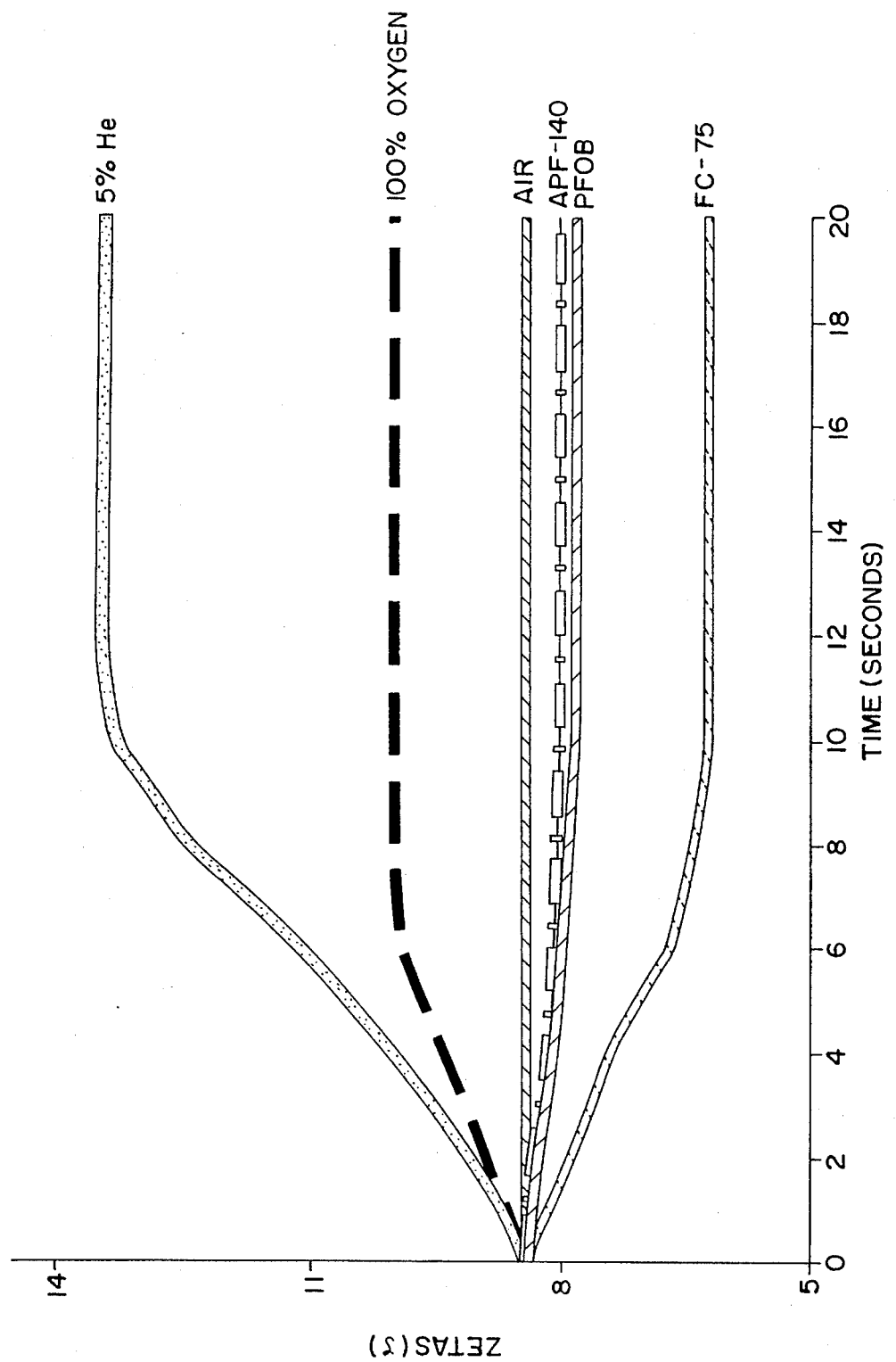
FIG. 9 graphically depicts zeta units and the time course until saturation for respiratory gases and for air saturated with different types of breathable liquid vapors.

FIGS. 3 and 4 show the basic instrumentation for performing thermal conductivity measurements which are employed in one embodiment of the invention to detect the amount of PFC in expiratory gas. FIGS. 5–7 provide background theory on a thermal conductivity related parameter (the zeta value) employed in the invention. FIGS. 8 and 9 relate to measurements for calibrating the thermal conductivity measurement apparatus in the invention. FIGS. 10, 11, 16 and 17 illustrate time studies of zeta values during theoretical patient sessions. Apparatus depicting the preferred embodiment of the novel breathable liquid elimination analysis system and methods are illustrated in FIGS. 12–15 and 18–23.

FIG. 3 is a schematic illustration of a portion of a preferred thermal conductivity detector/analyzer 10 employed in the invention. As noted above, the novel apparatus and method of one embodiment of this invention utilize the principle that different gases have different thermal conductivities. The principle of thermal conductivity, as applied to the thermal conductivity detector/analyzer 10 employed herein, follows.

Thermal conductivity, K, is a measure of the heat flow across a surface per unit time, divided by the negative of the rate of change of temperature with distance in a direction perpendicular to the surface. Expressed another way, thermal conductivity is the time rate of transfer of heat by conduction, through a unit thickness, across a unit area and for a unit difference in temperature. It can thus be expressed as watts per meter-Kelvin. It can be measured as calories per second per square centimeter for a thickness of 1 cm and for a difference of temperature of 1 degree Celsius, or calories/(cm)(sec.)(°C.).

Heat flow through a substance is thus proportional to the area of the material and the resultant temperature change over a given distance. This resultant temperature change is dependent on the material's molecular properties. These include, but are not limited to specific heat, vapor pressure, viscosity, rate of flow of mass, charge, temperature and conduit diameter. For a given material at a given temperature, these other properties are constant and the flow of heat over a given distance can be represented as thermal conductivity, K.

The thermal conductivity detector/analyzer 10 in FIG. 3 utilizes the above principles to assess the thermal conductivity, K, of PFCs and of respiratory gases. The detector/analyzer 10 utilizes a dual chamber design. Gas is flowed at a known rate and at a given temperature through chamber I (the active cell). Chamber II (the reference cell) is open to atmosphere with no flow therethrough. Thermistors 14 ($T_1$) and 16 ($T_2$) are heated to a known temperature. Gas flow in Chamber I changes the temperature assessed by $T_1$, relative to $T_2$. This temperature gradient is converted to an analog voltage, processed by an A/D converter and represented as a digital output. Thermistors 14 and 16 may be identical.

The scope of the invention also includes other thermistor configurations for detecting thermal conductivity.

The detector/analyzer 10 is calibrated by using air and 100% oxygen as the standards. These gases were chosen because of their already experimentally determined thermal conductive properties. Air, composed mostly of nitrogen, has a negligible thermal conductivity and thus registers an infinitesimally small temperature gradient between the thermistors 14 and 16. Thus, no voltage change occurs and the output is about 0.00 V. In contrast, the significantly higher thermal conductivity of 100% oxygen, produces a temperature gradient which results in an output of about 1.58 V. These two outputs are employed as the calibration standards.

The digital output signal of the detector/analyzer 10 is given as a zeta value or zeta unit (ζ) which is a proportionally related to the voltage resulting from a change in temperature per unit length. It reflects the concentration of a measured gas in a sample. The degree of temperature change is based on various thermodynamic properties intrinsic to the substance measured.

The zeta unit is equal to the voltage output described above, plus about 8.4. The zeta unit is thus merely an arbitrarily created value of thermal conductivity employed to generate trend charts and to set alarm and control functions.

FIG. 4 is an in vitro schematic illustration of a set-up for measuring the thermal conductivity of various gases using the detector in FIG. 3. The gas is input to pump 18 which uptakes the gas to headspace 20 of closed container or flask 22. The flask 22 is partially filled with PFC liquid 23. Vapor from the PFC liquid 23 saturates the gas flowing through the headspace 20. The saturated gas flows out of the flask 22 and through the thermal conductivity detector/analyzer 10.

The measuring system employed in FIGS. 3 and 4 utilize forced convection of gas through a conduit. During forced convection, heat is transferred from a solid heat source to the flowing gas by means of conduction and/or convection, depending on the flow characteristics. Flow can be characterized by the Reynolds number, symbolized as $N_{Re}$, a dimensionless number equal to the density of a fluid, times its velocity, times a characteristic length, divided by the fluid viscosity. In this system, it is expressed as:

$$N_{Re}=[(\rho/\mu)\times(4\dot{Q}/\pi d)] \quad \text{(Equation 1)}$$

where $\rho$ is the density of the gas (gm/ml), $\mu$ is the viscosity of the gas (gm/cm sec), $\dot{Q}$ is the flow rate (ml/sec), and d is the diameter of the conduit (cm). When the Reynolds number is greater than 3000, flow is considered turbulent. When the Reynolds number is less than 3000, flow is considered laminar.

The fluid dynamic properties of the fluid itself also dictate the amount of heat transfer in a system. These thermodynamic principles can be described by the dimensionless Prandtl number. In flow mechanics, the Prandtl number, symbolized as $Pr_m$, is equal to the kinematic viscosity divided by the molecular diffusivity. In thermodynamics, the Prandtl number, symbolized as $N_{Pr}$, is equal to the dynamic viscosity times the specific heat at constant pressure divided by the thermal conductivity. For purposes of this system, the Prandtl number is expressed as $$N_{Pr}=C_p\mu/k \quad \text{(Equation 2)}$$

where $C_p$ is the specific heat of the substance (cal/gm °C.), $\mu$ is the viscosity (gm/cm sec), and k is the thermal conductivity (cal/cm sec °C.).

Heat transfer can be evaluated by the dimensionless Nusselt number. In thermodynamics, the Nusselt number, symbolized as $N_{Nu}$, gives a measure of the ratio of the total heat transfer to conductive heat transfer, and is equal to the heat transfer coefficient times a characteristic length divided by the thermal conductivity.

In engineering practice, the Nusselt number for flow in conduits is usually evaluated from empirical equations based on experimental results. As a result, the forced-convection heat transfer relationship can be correlated to the following equation:

$$N_{Nu}=x\{(N_{Re})^a(N_{Pr})^b\} \quad \text{(Equation 3)}$$

where x is a numerical constant and a and b are experimentally determined exponents for the Reynolds number and Prandtl number, respectively. Flow conditions determine the value of a and b.

The Nusselt number for each respective gas measured in the system will determine the zeta value for that gas. The Nusselt number for respiratory gases was calculated based on the following equation:

$$N_{Nu}=(N_{Re})(N_{Pr}) \quad \text{(Equation 4)}$$

which simplifies to:

$$N_{Nu}=\rho C_p/k \quad \text{(Equation 5)}$$

A correlation was established between the Nusselt number and the measured zeta value in the form of the following equation (r=0.93, 1st order regression):

$$zeta=73.2-(15.6\ N_{Nu}) \quad \text{(Equation 6)}$$

FIG. 5 graphically depicts the zeta unit and Nusselt number for the following gases:

90% Air, 10% He
95% Air, 5% He
100% Oxygen
100% Room Air
100% Nitrogen

Measured zeta units were used to calculate the Nusselt number for different PFC-gas mixtures including:

Air fully saturated with APF-140 vapor
Air fully saturated with PFOB (perfluorooctylomide) vapor
Air saturated with Rimar™ vapor at saturation percentages of 100%, 75%, 50% and 25%
100% oxygen fully saturated with APF-140 vapor
100% oxygen fully saturated with PFOB vapor
100% oxygen fully saturated with Rimar™ vapor APF-140 is known generically as PP5 and Rimar™ is known generically as FC-75. Rimar™ is manufactured by Miteni Corp., Milano, Italy (represented in the U.S.A. by Mercantile Development Inc., Bridgetown, Conn.). FC-75 is also manufactured by 3M Company, St. Paul, Minn.

Since each PFC has a different vapor pressure, each will possess different percentages of volume in saturated gas. For example, FC-75 which has a vapor pressure of 57 mm Hg will occupy 8.0% (57 mm Hg/713 mm Hg) of a saturated gas, while PFOB with a vapor pressure of 11 mg Hg will occupy only 1.54% of a saturated gas. Therefore, the Nusselt number for a PFC-gas mixture must be multiplied by the volume percent of the PFC vapor. This will accurately assess the percent difference from the carrier gas only.

FIG. 6 graphically depicts zeta values for different carrier gases in their unsaturated state and when fully saturated by three different PFC vapors. The graph shows how the zeta value varies based on the volume percent of the PFC vapor in the carrier gas. FIG. 6 demonstrates that the percent change from baseline by the addition of various PFCs is identical for three different carrier gases (nitrogen, oxygen and air). Theoretically, this relationship can be applied to any carrier gas.

FIG. 7 graphically depicts zeta values for different volume dilutions of room air saturated with FC-75 type PFC vapor. More specifically, volumes of room air were diluted with varying percentages of FC-75 vapor and their respective zeta values recorded. Serial dilution of room air with incremental volumes of FC-75 vapor was found to be generally linear from 0% (unsaturated room air) to about 100% (fully saturated air). The data point at 0.00% Vol represents unsaturated air. The data point at about 0.063% Vol represents fully saturated air. The data points are extrapolated to generate a straight line function, zeta=a(Vol %)+b, where a is the slope of the line and b is a constant.

This in vitro relationship may be extrapolated to in vivo data. As the volume of PFC vapor diluted in air decreases, the zeta value approaches that of 100% carrier gas. Thus, as PFC-gas interaction in the lungs wanes, the percentage volume of PFC vapor in the expired respiratory gas decreases, and the zeta value will approach about 8.4 $\zeta$.

This relationship allows an operator to monitor the volume (i.e., liquid amount) of PFC liquid in the lungs which is lost over time from the respiratory process during partial liquid ventilation. This information is employed to control the replenishment of the PFC liquid in the lungs. Alternatively, it is employed as a double-check on the PFC information derived by monitoring the zeta trend line, as will be described more fully below.

To convert the percentage volume information in air (as derived from the measured zeta value), the percentage volume is first converted into the PFC liquid amount value by multiplying the percentage volume in air by a constant representing the liquid amount (in liters) of PFC in a known volume of PFC vapor at the measured temperature. During the partial liquid ventilation session, the instantaneous flow rate of expired respiratory gas and zeta value is continually measured and recorded. This information allows a computer to generate the instantaneous rate of loss of PFC liquid. The instantaneous rate of loss of the PFC liquid is then integrated over time to obtain the total loss of PFC liquid by volatilization. The total loss value is then adjusted to account for the small amount of PFC liquid lost through evaporation into the bloodstream.

One algorithm suitable for determining PFC volume loss is as follows:

$$\text{PFC loss} = V_R \times (\% \text{ Vol of PFC}) \times \text{time} \times C_{LV} \qquad \text{(Equation 7)}$$

where $V_R$ is the volumetric ventilation in volumetric units/per time. $V_R$ is equal to the oxygenator pump flow when quantifying PFC loss from a total liquid ventilation system. $V_R$ is equal to minute ventilation when quantifying PFC loss from a patient (also known in the art as $V_M$). $C_{LV}$ is a liquid/vapor conversion factor. Previous experiments have shown, for example, that 86 ml of PFOB vapor equals 1 ml of neat fluid and that this relationship is constant over a temperature range of zero degrees Celsius to 37 degrees Celsius. This relationship is based on calculation of the mole fraction of PFC in a carrier gas where:

| Mole fraction | = | (22.4 moles of gas/liter) × | (Equation 8) |
|---|---|---|---|
| | | (300° Kelvin/273° Kelvin) × | |
| | | (Specific Gravity/Molecular weight | |
| | | (in grams)) | |

The % Vol of PFC in Equation 7 is dependent upon the percent saturation of carrier gas and the temperature of the vapor. As is well known in the art, this value must also be corrected for absolute pressure and water vapor pressure variations. To determine the PFC loss rate, the time is deleted from Equation 7.

Experimental data has shown that the presence of carbon dioxide in the expired respiratory gas does not significantly alter the zeta values from what they would be if the patient were exhaling only pure air. If the patient is breathing pure oxygen instead of air, a different straight line zeta function is employed. Once the percentage volume of PFC is determined, the calculations proceed exactly the same as described above. Likewise, a different straight line zeta function is employed if a different type of PFC is used.

FIG. 8 graphically depicts the standard calibration for the detector/analyzer 10. As noted above, air and 100% oxygen are employed as the standards. Room air is flowed through the detector/analyzer 10 in the time period from A to B, followed by 100% oxygen (time period from B to D), followed by a return to room air.

FIG. 9 graphically depicts the zeta units for selected respiratory gases and for air saturated with different types of PFC vapors. The time course until saturation is also included.

Figure 10:
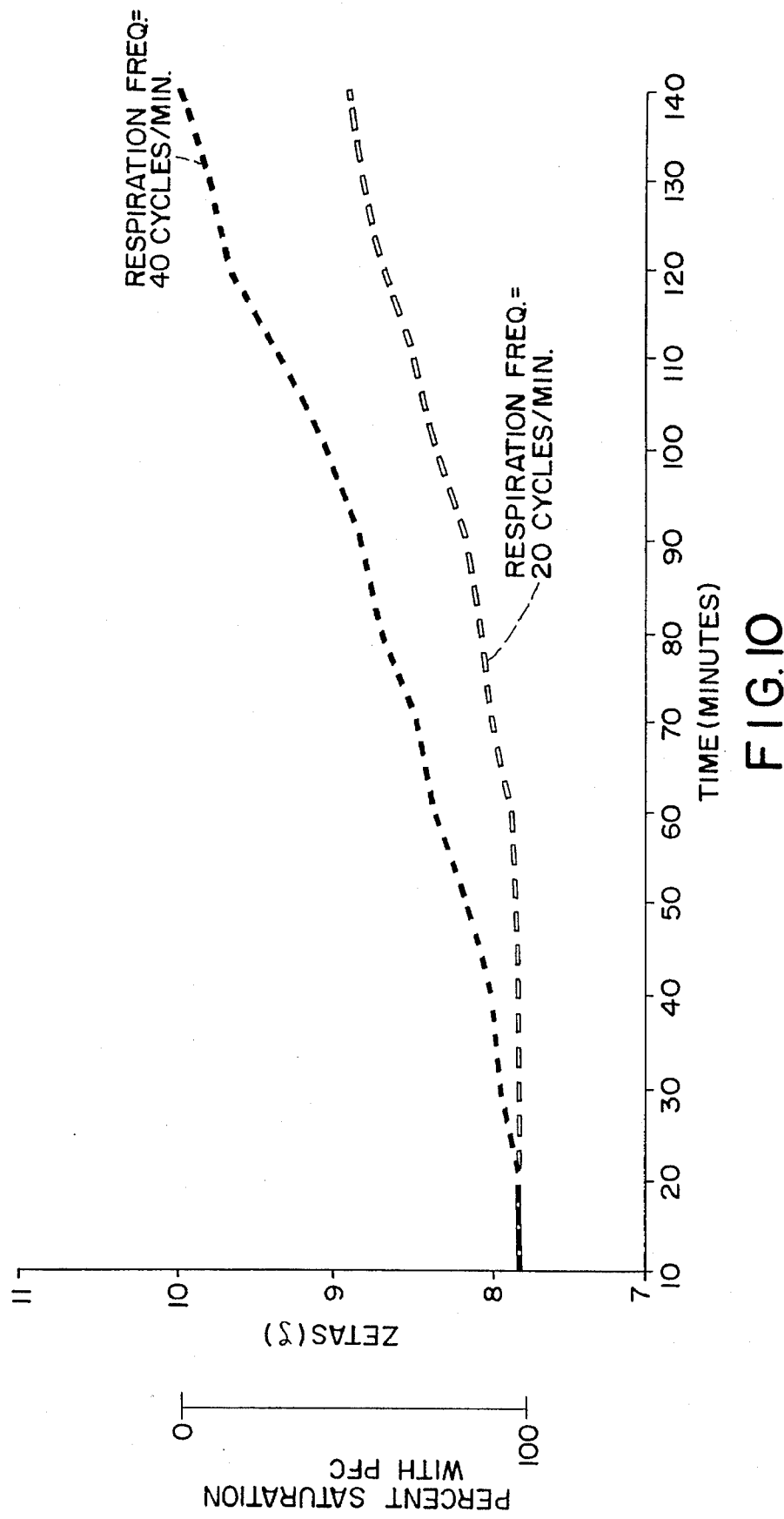
FIG. 10 graphically depicts the effect of breathing frequency on volatilization of a breathable liquid.

FIG. 10 graphically depicts the effect of breathing frequency (i.e., respiration rate) on PFC volatilization. In this scenario, the respirator supplies pure oxygen and the patient's lungs are filled with FC-75 type PFC liquid. The zeta value begins at 100% saturation since oxygen in the expired respiratory gas is fully saturated with FC-75 vapor. As time progresses, the amount of liquid PFC in the lungs slowly depletes as it volatilizes. Eventually, the saturation level of the oxygen begins to decline, thereby causing the zeta value to approach the value for unsaturated pure oxygen (i.e., 10.0 $\zeta$). As expected, the trend upward to the unsaturated oxygen value is faster for a breathing frequency of 40 cycles/min than for a breathing frequency of 20 cycles/min. Since a faster breathing frequency results in greater alveolar ventilation, this graph indicates that PFC volatilization is positively correlated with alveolar ventilation. That is, the greater the alveolar ventilation, the greater the PFC volatilization.

Figure 11:
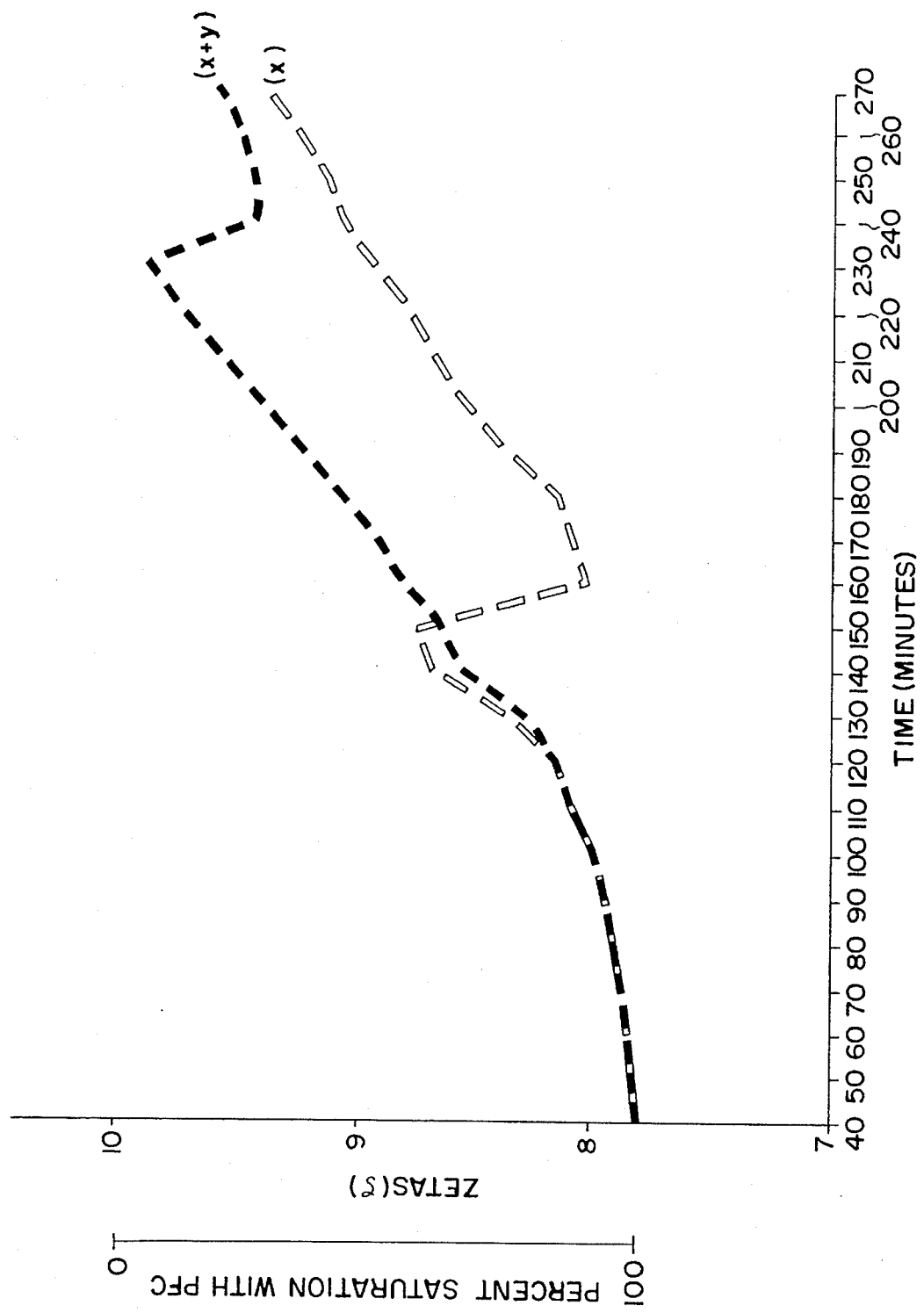
FIG. 11 graphically depicts the effect of breathing frequency on volatilization of a breathable liquid and also shows the time dependence of patient repositioning on the rate of change of the zeta value.

FIG. 11 graphically depicts the effect of breathing frequency on PFC volatilization and also shows the time dependence of patient repositioning on the rate of change of the zeta value. In this scenario, the respirator supplies pure oxygen and the patient's lungs are filled with FC-75 type PFC liquid. The zeta value begins at 7.8 $\zeta$ (100% saturation) since the oxygen in the expired respiratory gas is fully saturated with FC-75 vapor. As time progresses, the amount of liquid PFC in the lungs slowly depletes as it volatilizes. The zeta value thus slowly approaches 10.0 $\zeta$ (0% saturation), in the same manner as demonstrated in FIG. 10.

Turning first to the trend line for a breathing frequency of x cycles/min, the trend line suddenly takes a sharp turn upward at about 14 minutes. That is, $d\zeta/dt$ sharply increases, thereby indicating that the saturation level of the oxygen is dropping rapidly instead of gradually. This indicates that the amount of interaction in the lungs between the liquid PFC and oxygen has suddenly dropped. One possible reason for this sudden drop is that the liquid PFC has become maldistributed in the patient's lungs. At about 150 minutes, the patient is repositioned to attempt to more evenly distribute the liquid PFC in the lungs. Shortly thereafter, the zeta value sharply drops back down and continues along at a more steady upward trend line. This indicates that the liquid PFC was, indeed, maldistributed in the lungs. After this situation was corrected, the amount of interaction in the lungs between the liquid PFC and oxygen significantly increased, thereby increasing the saturation level of the oxygen and lowering the zeta value of the expired respiratory gas.

Turning next to the trend line for a breathing frequency of x+y cycles/min, it is relatively steady until shortly after about 230 minutes. At this point, the patient is repositioned and the zeta value drops shortly before resuming a steady upward trend. In this instance, the maldistribution of the liquid PFC occurred so gradually that the trend line showed no rapid increase, as in the x cycle/min trend line.

Figure 12:
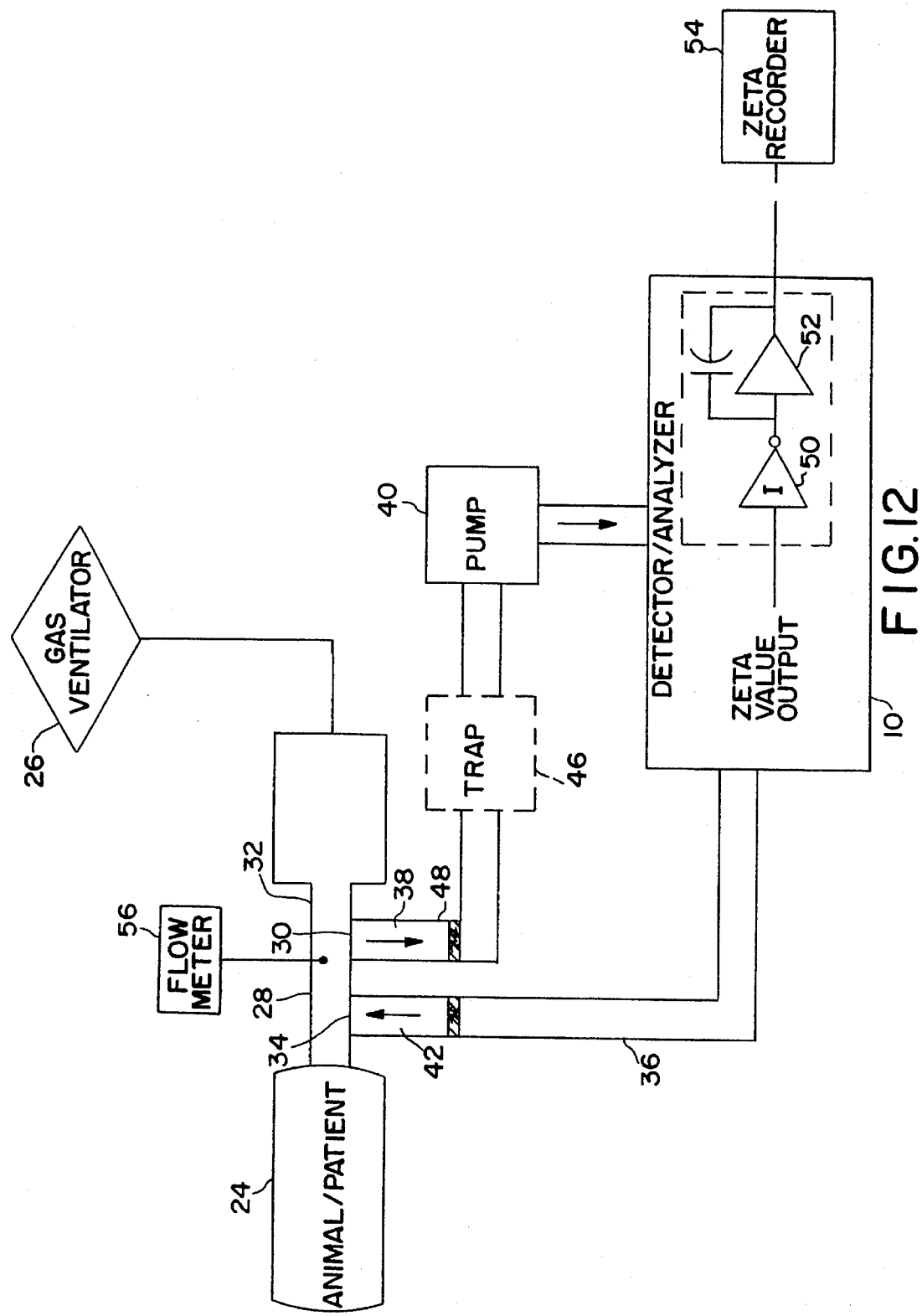
FIG. 12 shows an in vivo schematic diagram of a PFC elimination analysis system for sampling respiratory gas in a partial liquid ventilation process.

FIG. 12 shows an in vivo schematic diagram of a PFC elimination analysis system for sampling respiratory gas in a partial liquid ventilation process. The trachea of a living being, such as an animal or patient 24, is connected to a respiratory gas ventilator 26 through an endotracheal tube 28 such as a HI-LO JET® tracheal tube, manufactured by Mallinckrodt Medical, Inc., St. Louis, Mo. The open end of this tube 28 is connected to the ventilator 26 which maintains the function of breathing by pushing ventilating gases in and out of the patient's lungs. One version of this tube 28 has two different side ports. A first port 30 is proximal to the tube's median 32 and the second port 34 is distal to the median 32. The first port 30 is in fluid communication with the input of a sampling path 36 and the second port 34 is in fluid communication with the output of the sampling path 36. The sampling path 36 thus is a closed loop, continuous flow path for continuously sampling the respiratory gas flowing through the tube 28 and returning the sampled gas back into the tube 28. Accordingly, no net gas is added or removed from the patient 24. This scheme also does not cause any physiologic perturbations such as a lowered partial pressure of oxygen or an elevated partial pressure of carbon dioxide.

The sampling path 36 comprises, in series order, inflow tube 38, circulating pump 40, thermal conductivity detector/analyzer 10 and return tube 42. The inflow tube 38 allows for fluid communication between the circulating pump 40 and the first port 30, whereas the return tube 42 allows for fluid communication between the detector/analyzer 10 and the second port 34. The detector/analyzer 10 outputs a zeta value, as described above. A recorder 44 is connected in parallel to the detector/analyzer 10 to record the zeta value calculated in the detector/analyzer 10 at discrete time periods.

The sampling path 36 may optionally include a fluid trap 46 between distal end 48 of the inflow tube 38 and the input end of the pump 40 for preventing lung fluid, mucus or other liquid or solid substances from entering the pump 40 and the detector/analyzer 10. The detector/analyzer 10 may also optionally include a series connection of an inverter 50 and high pass filter 52 to provide positive signal deflection and clarification of the output signal before it's output is sent to zeta recorder 54.

FIG. 12 also shows flowmeter 56 for continuously measuring the instantaneous flow rate of expired respiratory gas. The instantaneous flow rate the % saturation PFC value at each instant is sent to a computer to generate the instantaneous rate of loss, as well as total volume loss of PFC liquid from the lungs. Subsequent figures show applications of the flowmeter 56.

Figure 13:
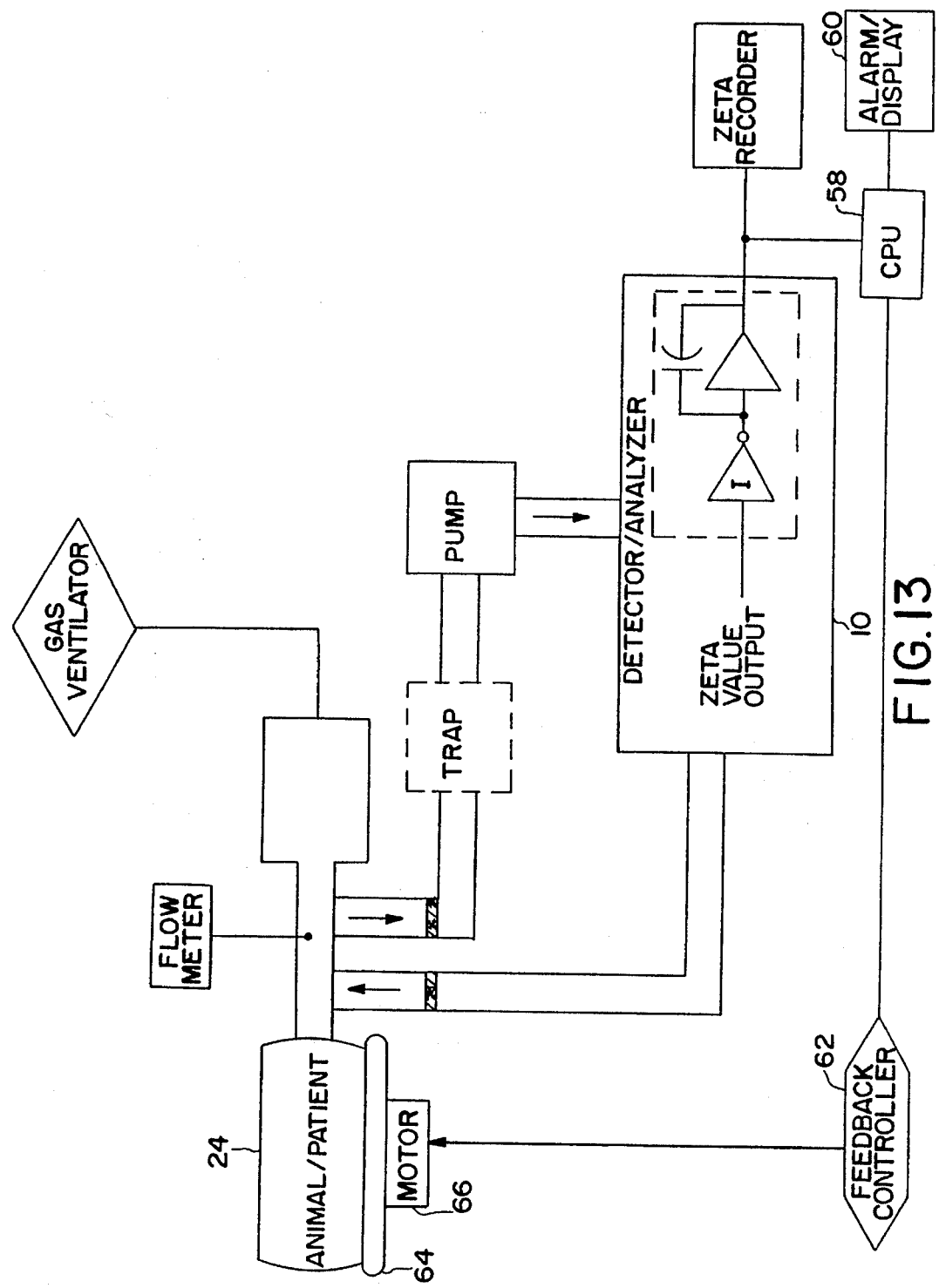
FIG. 13 shows a system as in FIG. 12 which includes feedback means for controlling the physical position of a patient.
Figure 14:
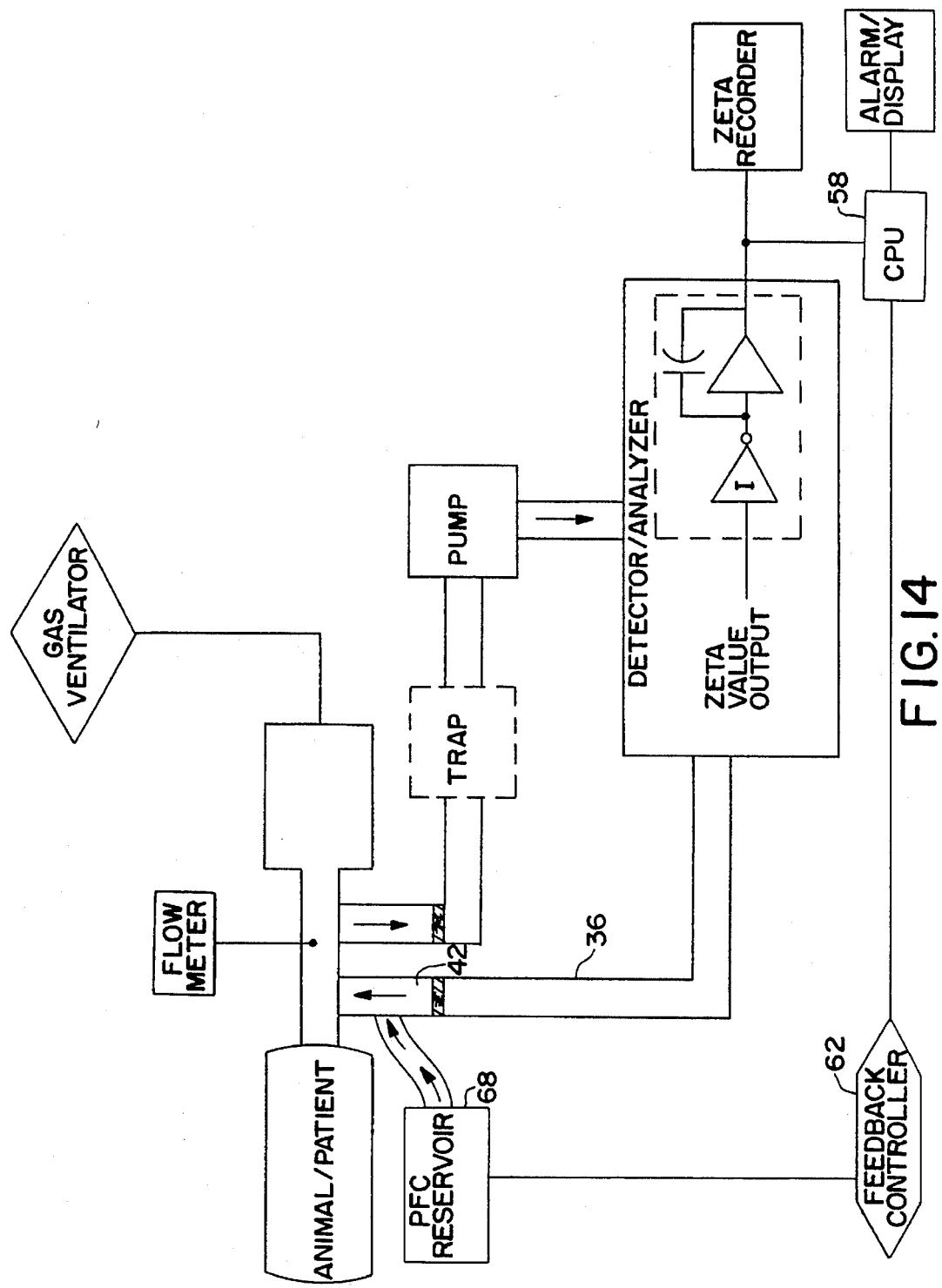
FIG. 14 shows a system as in FIG. 12 which includes feedback means for controlling a replenishment supply of PFC.
Figure 15:
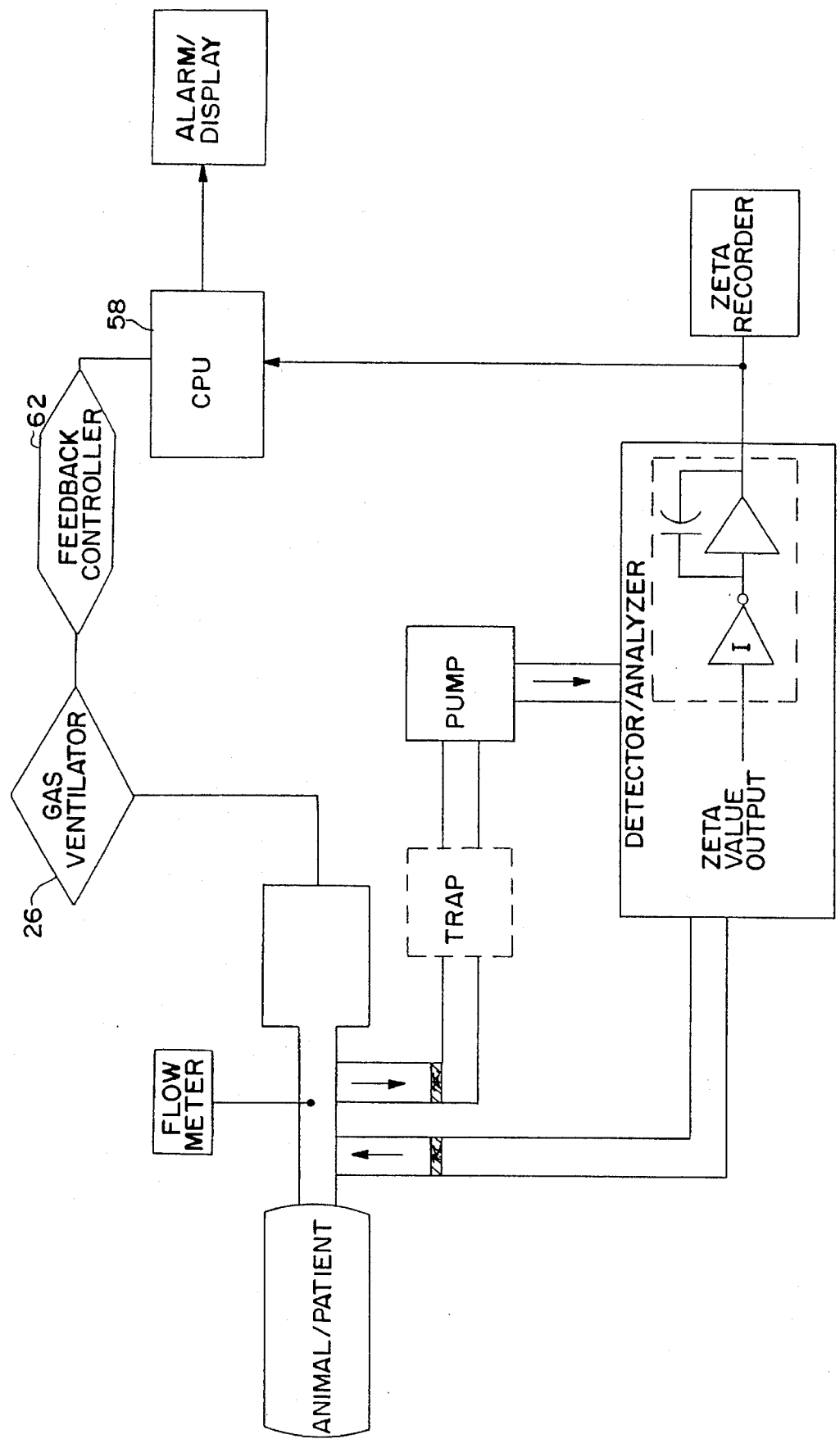
FIG. 15 shows a system as in FIG. 12 which includes feedback means for controlling the operation of a ventilator in the FIG. 12 system.

FIGS. 13–15 show how the digital zeta value output of the detector/analyzer 10 is employed to alarm an operator and provide selected feedback control functions. In FIG. 13, the zeta value controls the physical position of the patient 24. In FIG. 14, the zeta value determines whether the return tube 42 should draw from a reservoir of PFC liquid to replenish the PFC in the patient's lungs. In FIG. 15, the zeta value controls the operation of the ventilator 26.

Turning to FIG. 13, the zeta value is connected to the input of central processing unit (CPU) 58. The CPU 58 is preprogrammed with information for determines whether the operator should be alerted via audible or visual alarm/display 60 that the zeta value, or the time rate of change of the zeta value ($d\zeta/dt$), is outside of a given range. The CPU 58 is also preprogrammed with instructions on how to respond to out of range conditions and to output appropriate control signals to feedback controller 62. One possible response is to alert the operator via the alarm/display 60 to reposition the patient's bed 64 or to automatically control a bed positioning motor 66 to perform that function.

FIG. 14 shows the feedback controller 62 connected to a reservoir 68 of PFC. If the bed repositioning does not improve the PFC-gas interaction, the CPU 58 instructs the feedback controller 62 to release more PFC into a patient's lungs by allowing PFC from the reservoir 68 to enter the return tube 42 of the sampling path 36.

FIG. 15 shows the feedback controller 62 connected to the ventilator 26 to cause the ventilator 26 to increase its respiration rate or inspiratory pressures.

The feedback control functions shown in FIGS. 13 and 14 are most appropriate during partial liquid ventilation, whereas the function shown in FIG. 15 is most appropriate while weaning a patient from total liquid ventilation to conventional gas ventilation. When a patient is weaned from total liquid ventilation, a residual amount of PFC liquid will remain in the lungs. Eventually, the residual PFC will completely volatilize. However, if the residual PFC is taking too long to volatilize (as indicated by a zeta value that is taking too long to reach the value for unsaturated pure ventilation gas), the feedback controller 62 may cause the ventilator 26 to increase its respiration rate or inspiratory pressures. This will increase the amount of alveolar ventilation, and thus will more rapidly promote PFC volatilization.

Figure 16:
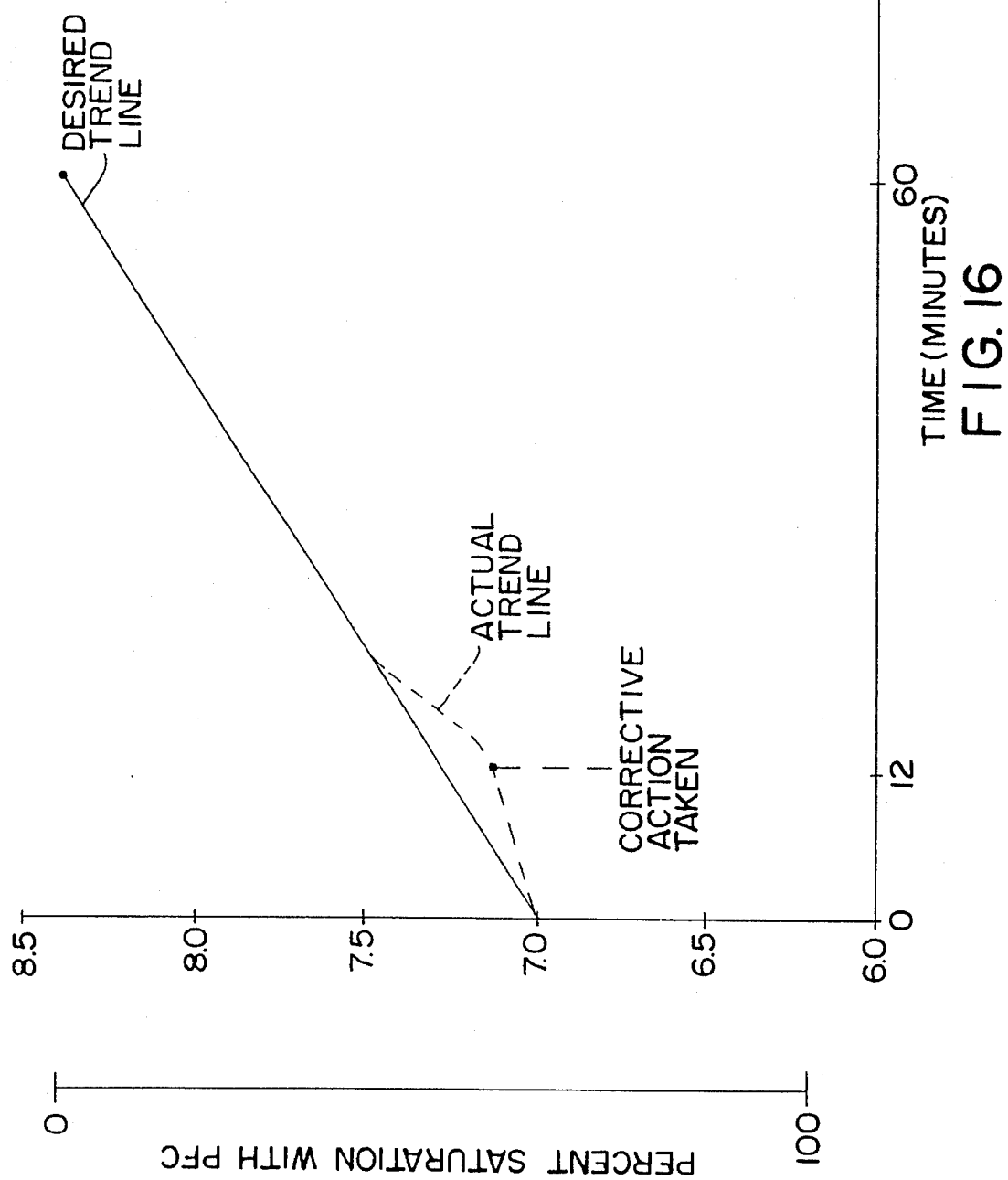
FIG. 16 graphically depicts zeta values during a weaning process while employing the system of FIG. 15.

The application of the control function in FIG. 15 is best understood with respect to FIG. 16 which graphically depicts zeta values during the weaning process. At zero minutes, liquid ventilation with FC-75 type PFC liquid has ceased and conventional gas ventilation with room air has begun. The residual PFC in the patient's lungs volatilizes and partially saturates the expired respiratory gas. This results in a zeta value of about 7.0 $\zeta$ which is between the 8.4 $\zeta$ value of room air and the 6.2 $\zeta$ value of air fully saturated with FC-75. As time progresses, the amount of liquid PFC in the lungs slowly depletes as it volatilizes and evaporates therefrom. Since no PFC is being added, the zeta value trends upward to 8.4 $\zeta$ (the value for unsaturated, room air). Since the weaning process from total liquid ventilation to conventional gas ventilation should be relatively quick (e.g., about 30–60 minutes), the solid trend line shows the desired progression of the zeta value. However, if volatilization is occurring too slowly, due to insufficient alveolar ventilation, the trend line will appear as shown in the dashed line. Mathematically speaking, this occurs when the slope of the trend line, $d\zeta/dt$, is below a predesired value. The CPU 58 is programmed to detect this condition and to increase the respiratory rate or inspiratory pressure of the ventilator 26. In the weaning process shown in FIG. 16, the CPU 58 determines after about 12 minutes that the volatilization is proceeding too slowly. Corrective action is taken and shortly thereafter, the dashed trend line merges with the desired solid trend line.

From the information in the FIG. 16 trend line, the amount of PFC left in the lungs and the time course of volatilization is easily derived (using the algorithm in Equation 7). Heretofore, there was no accurate or even theoretical means of correctly assessing these parameters.

Figure 17:
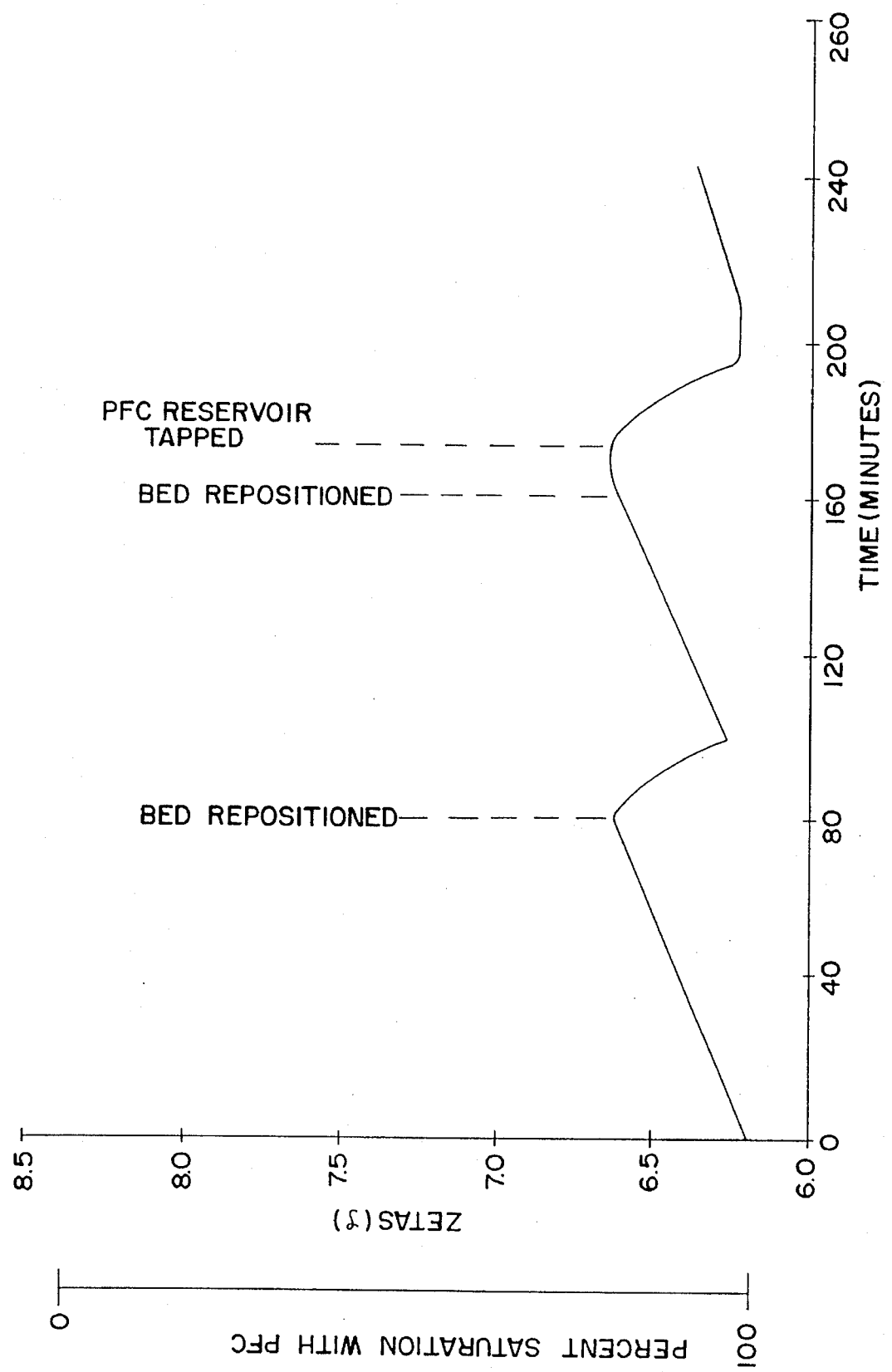
FIG. 17 graphically depicts zeta values during a hypothetical partial liquid ventilation session while employing the systems of FIGS. 13 and 14.

The application of the control functions in FIGS. 13 and 14 are best understood with respect to FIG. 17 which graphically depicts a hypothetical partial liquid ventilation session. In the scenario depicted in FIG. 17, the respirator supplies air and the patient's lungs are filled with FC-75 type PFC liquid. The zeta value begins at 6.2 $\zeta$ since the air in the expired respiratory gas is fully saturated with FC-75 vapor.

As time progresses, the amount of liquid PFC in the lungs slowly depletes as it volatilizes and evaporates therefrom. If the ventilation set-up is left alone as in the set-up depicted in FIG. 10, the zeta value would eventually approach and stabilize at 8.4 $\zeta$ (the value for unsaturated, room air). However, unlike the test set-up in FIG. 10, measures are continuously taken to maintain the zeta value at, or near, the fully saturated value of 6.2 $\zeta$. This is because when the air is fully saturated, maximum gas-PFC interaction, and thus maximum alveolar ventilation occurs. Accordingly, the trend line will be relatively flat (average $d\zeta/dt=0$) during the ventilation session. (For illustration purposes, the zeta value scale in FIG. 17 is greatly exaggerated, thereby causing the slope of the trend line to appear steeper than it really is.)

During the first 80 minutes of the session, the zeta value gradually rises from 6.2 $\zeta$. The CPU 58 in FIG. 13 is set to take corrective measures once the zeta value exceeds about 6% of its desired value. Thus, when the zeta value reaches 6.6 $\zeta$ at 80 minutes, the CPU 58 alerts the operator via alarm/display 60 with a prompt such as, "PFC LEVEL OUT OF RANGE REPOSITION PATIENT OR ADD ADDITIONAL PFC." Alternatively, the feedback controller 62 will automatically send a signal to the bed positioning motor 66 to reposition the patient. In the hypothetical session depicted in FIG. 17, varying the bed position returned the zeta value back to an acceptable amount.

At 160 minutes, the zeta value is again out of range. Bed repositioning is attempted, but this time it fails to bring the value back into range. The CPU 58 detects that the zeta value is not declining and determines that it is necessary to add additional PFC. The operator is alerted to perform this function, or the feedback controller 62 automatically releases more PFC into a patient's lungs, as described in FIG. 14.

Although the systems in FIGS. 13–15 are illustrated separately, it should be understood that a single system may include more than one type of feedback control.

PFC RECOVERY

Breathable liquid such as PFC volatilizes from a diffuser/condenser circuit during total liquid ventilation. Expired breathable liquid is scrubbed to remove the carbon dioxide, reoxygenated and returned to the lungs during a subsequent inspiratory breathing stage. Currently, the vaporized breathable liquid in the expiratory liquid is not recovered during this process. Instead, it is vented to the environment. Accordingly, the system must periodically add more breathable liquid from a storage reservoir. As noted above, the loss of breathable liquid in this process is costly.

Figure 18:
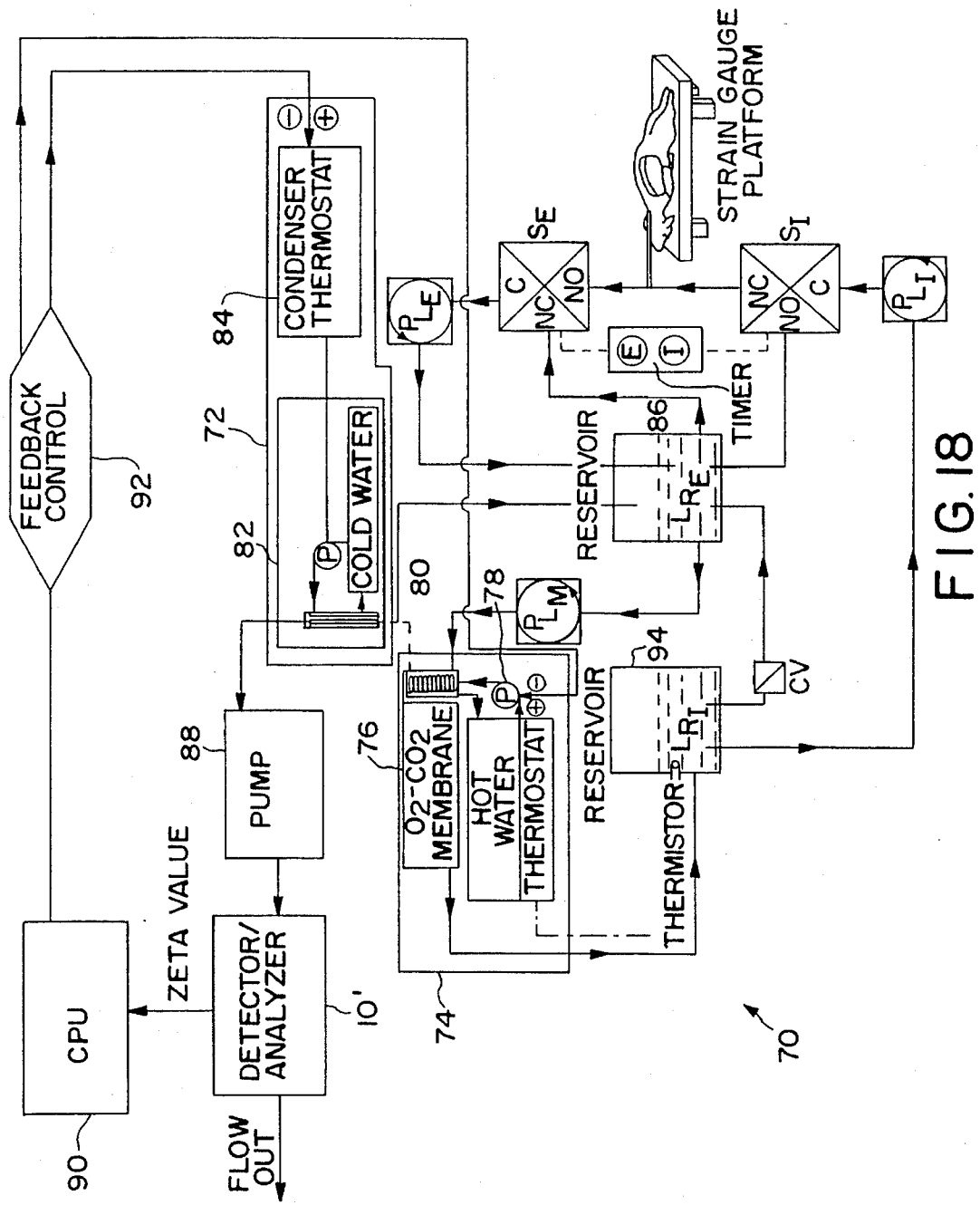
FIG. 18 shows a total liquid ventilation system which includes PFC detection and recovery apparatus.

FIG. 18 shows a total liquid ventilation (TLV) system 70 employing PFC as the breathable liquid. The system 70 recovers PFC from volatilized breathable liquid which may potentially escape to the environment. Furthermore, the system 70 employs the thermal conductivity of the PFC, as measured in zeta units, to monitor and control the efficiency of the recovery process.

The TLV system 70 includes condenser circuit 72 connected in parallel to oxygenator/diffuser 74. The oxygenator/diffuser 74 includes an $O_2$—$CO_2$ Membrane 76, as is well-known in the art, for removing dissolved gas from expiratory liquid flowing therethrough. As PFC is pumped through the oxygenator/diffuser 74 by pump 78, the corresponding PFC vapor travels to the condenser circuit 72 via path 80. The condenser circuit 72 includes a condenser 82 to capture the PFC vapor via cold condensation and a condenser thermostat 84. The recovered PFC fluid is then re-introduced into PFC expiratory reservoir 86.

Two important factors determine the amount of PFC vapor lost from the TLV system 70 (and thus determine the efficiency of the TLV system 70 in recovering PFC). One important factor is pump flow through the oxygenator/diffuser 74. Another important factor is the operating condition of the elements of the condenser circuit 72. For example, PFC vapor loss is proportional to the oxygenator/diffuser 74 pump flow. The TLV system 70 employs thermal conductivity detector/analyzer 10' to track the vapor recovery process. A pump 88 draws off gas samples from the output path of the condenser 82 and flows them through the detector/analyzer 10' to obtain a voltage level correlated to a zeta value. The zeta value is sent to CPU 90 for analysis. If the CPU 90 determines that the zeta value is outside of a predetermined range, it sends a signal to feedback controller 92 to take appropriate remedial action. One type of action is to increase or decrease the pump flow in the pump 78 of the oxygenator/diffuser 74. Another type of action is to modify operating conditions of the condenser circuit 72 elements. Continuous feedback control determines the most efficient pump flow amount and condenser operating conditions. Of course, the goal of the feedback loop is to minimize the amount of PFC vapor in the drawn off gas sample (as determined by the zeta value) without compromising other functions of the TLV system 70.

In the embodiment of the invention shown in FIG. 18, the condenser circuit 72 includes a condenser thermostat 84 with a variable set point. Thus, the operating condition modified in this embodiment is the set point of the condenser thermostat 84. It is raised or lowered to achieve optimum vapor recovery. Other known ways to improve the efficiency of the condenser 82 include applying ultrasound or vibrations thereto. Although the disclosed embodiment adjusts only the condenser thermostat 84, the scope of the invention includes all known methods for varying the operating conditions of the condenser circuit elements. Thus, instead of, or in addition to, adjusting the condenser thermostat 84 in response to a feedback control signal, the ultrasound or vibration level may be adjusted.

The recovery of PFC is easy to monitor with this system. The total amount of liquid PFC in expiratory reservoir 86 and inspiratory reservoir 94 will remain constant if PFC recovery is 100% efficient. The output from reservoir level indicators (not shown) are connected to the CPU 90 to monitor recovery amounts. If recovery efficiency drops significantly below 100%, the reservoirs will need regular refilling. The refill rate will be proportional to the recovery efficiency.

Figure 19:
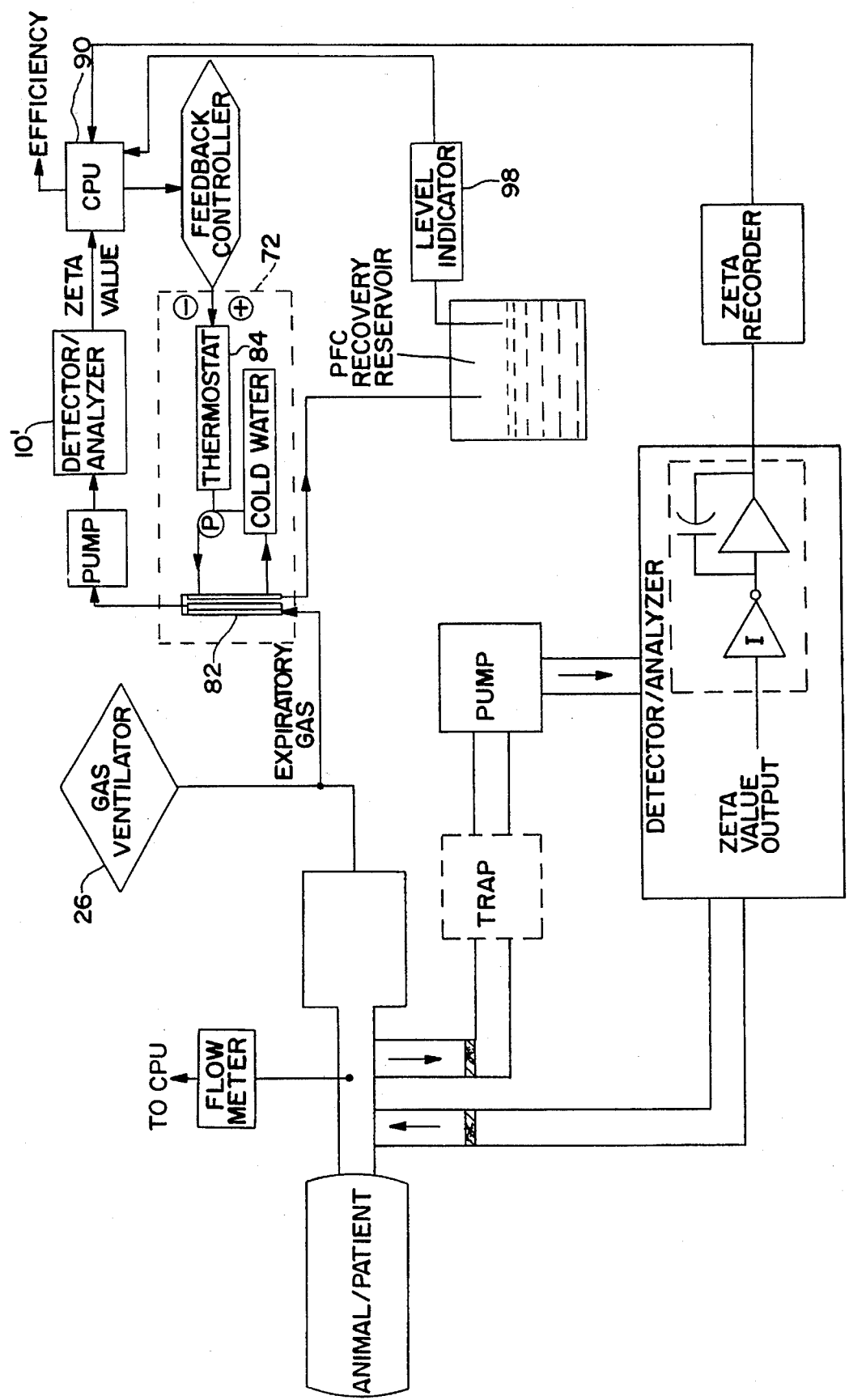
FIG. 19 shows a partial liquid ventilation system which includes PFC recovery apparatus.

FIG. 19 shows a partial liquid ventilation (PLV) system 96 employing PFC as the breathable liquid. The system 96 employs the same condenser circuit 72 of FIG. 18 to recover volatilized PFC from expired respiratory gas. Likewise, the system 96 employs the thermal conductivity of the PFC vapor to monitor the efficiency of the PFC recovery process and adjust the operating conditions of the condenser circuit 72 elements.

The PFC recovery efficiency is measured in one of two ways. In one scheme, the PFC vapor is detected in the sampling path 36 and in the output path of the condenser 82. The zeta values of the two samples are compared to determine how well the condenser circuit 72 is recovering the PFC vapor. In another scheme, the zeta values of the samples detected in the output path of the condenser 82 are employed (see the calculation method described above with respect to FIG. 7) to determine the total amount of liquid PFC not being recovered. The unrecovered liquid amount is compared to the recovered amount (i.e., the liquid amount of PFC condensed by the condenser 82) to determine the recovery efficiency. The output from reservoir level indicator 98 is connected to the CPU 90 to monitor recovery amounts. Of course, the CPU 90 employs the zeta value from detector/analyzer 10' to continuously adjust the operating conditions of the condenser circuit 82 for maximum achievable efficiency.

END-EXPIRATORY GAS SAMPLING

Figure 20:
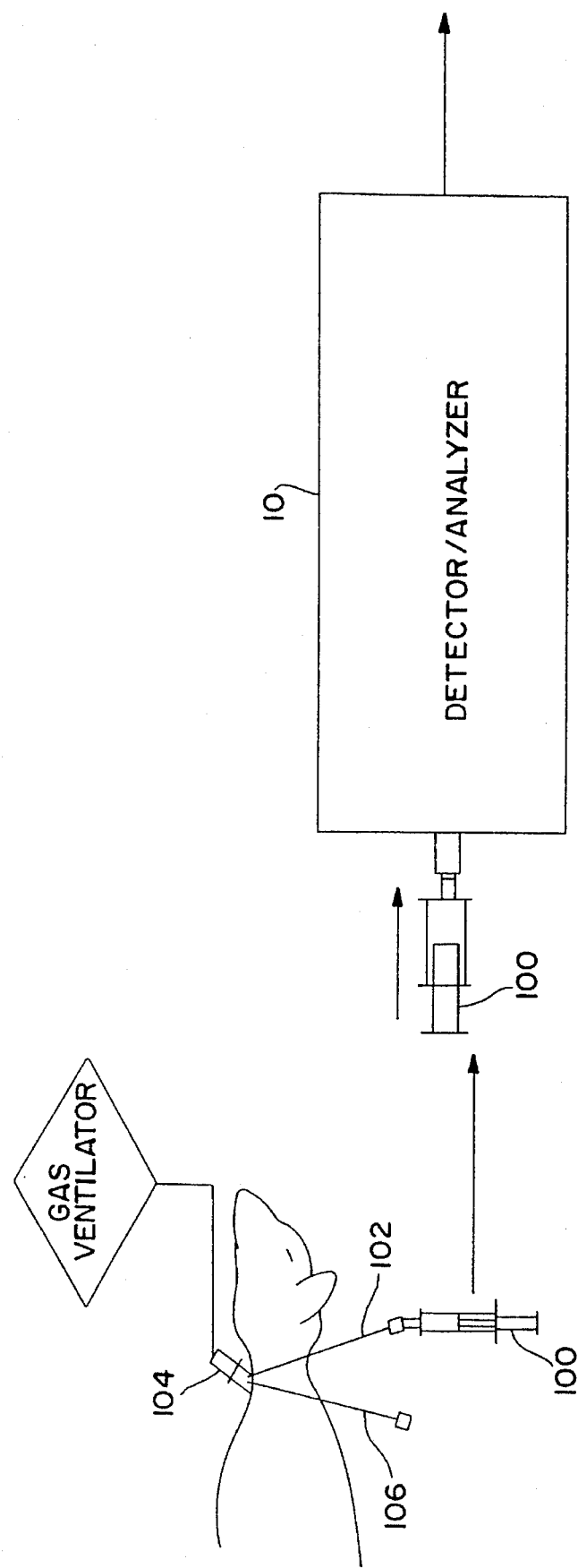
FIG. 20 shows a measurement detector/analyzer employed for end-expiratory gas sampling during partial liquid ventilation.

FIG. 20 shows how the thermal conductivity detector/analyzer 10 is utilized for end-expiratory gas sampling during partial liquid ventilation. At the end of expiration, a volumetric syringe 100 with headspace draws off expiratory gas from inflow tube 102 connected to endotracheal tube 104. (Endotracheal return tube 106 is left unconnected.) The syringe contents are then injected at a constant flow rate into the detector/analyzer 10 and the zeta value is determined. The zeta value is then extrapolated to determine PFC-gas interaction or used for respiratory gas measurement. In cases of respiratory compromise, this may be the preferred method of analysis because sampling time is minimal.

SOLENOID REBREATHING

Figure 21:
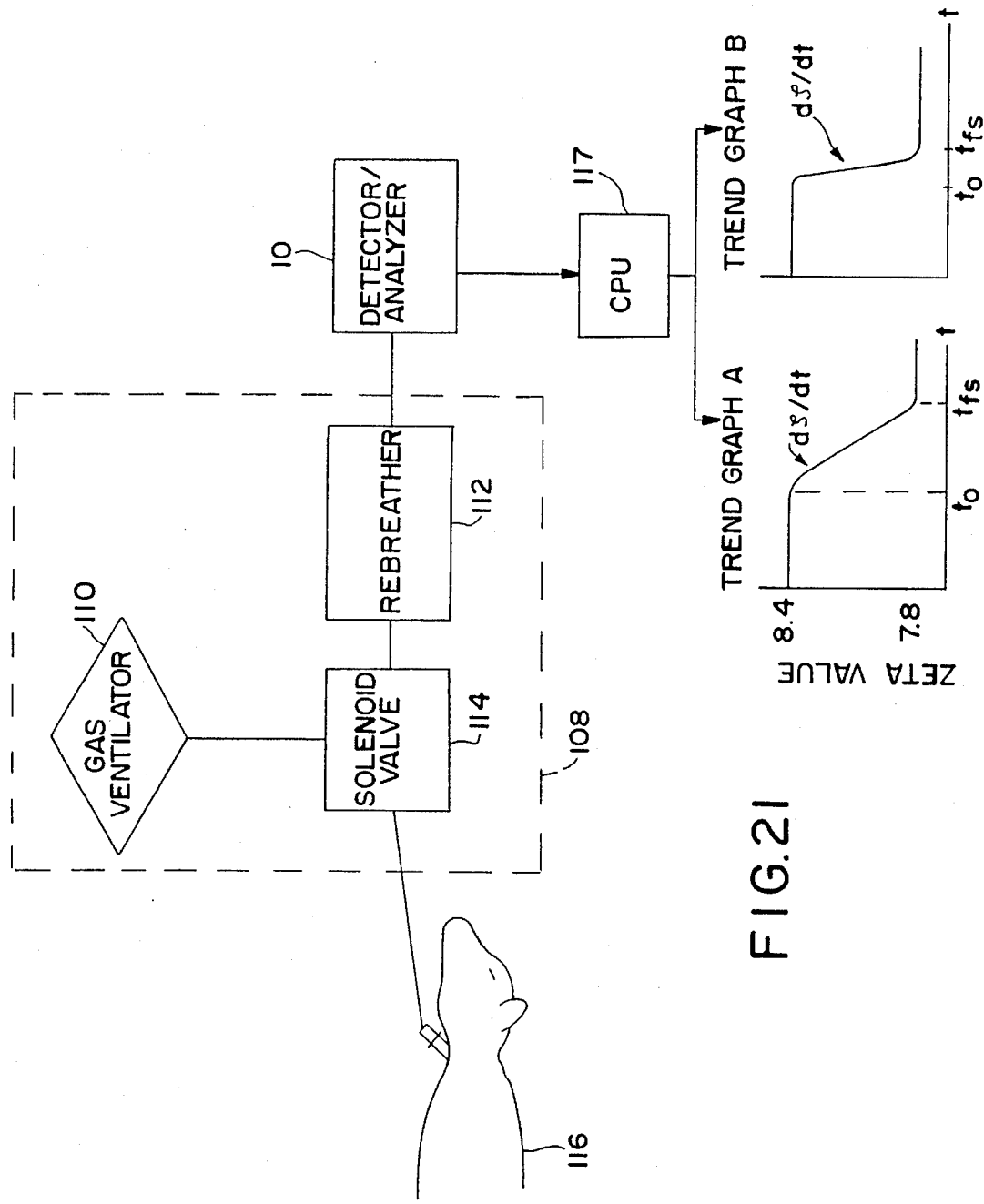
FIG. 21 shows a solenoid rebreathing apparatus set-up which assesses PFC-gas interaction during a partial liquid ventilation session.

FIG. 21 shows how PFC-gas interaction is assessed using a solenoid rebreathing apparatus set-up 108 during a partial liquid ventilation session. The apparatus 108 includes ventilator 110, rebreather 112 and three-way solenoid valve 114 connected therebetween. Animal or patient 116 inspires and expires ventilation gas through the solenoid valve 114. The solenoid valve then opens to the rebreather 112 and simultaneously closes the pathway to and from the ventilator 110. PFC vapor from PFC volatilization flows into the gas in the rebreather 112. Eventually, that gas becomes saturated by PFC vapor. After saturation, the solenoid valve 114 switches back to the ventilator 110 mode. Thermal conductivity detector/analyzer 10 measures the gas and sends a zeta value output to CPU 117. The CPU 117 calculates the rate of change of the zeta value over time, $d\zeta/dt$, which provides an indirect measure of the PFC-gas interaction. The instantaneous slope is a function of the PFC-gas interaction. The faster that the rate reaches equilibrium, the greater the PFC-gas interaction. Thus, a large slope indicates significant interaction, whereas a small slope indicates relatively little interaction. This interaction efficiency measurement may be used in place of the in-line system depicted in FIG. 12.

FIG. 21 shows two trend graphs A and B which represent different partial liquid ventilation sessions. The breathable liquid is PFOB. In trend graph A, the trend line slope ($d\zeta/dt$) between the time that the solenoid valve 114 switches between the ventilator 110 and the rebreather 112, $t_0$, and the time of full saturation, $t_{fs}$, is significantly less than the trend line slope between those same points in time in trend graph B. Thus, the PFC-gas interaction in session B is greater than in session A. In the system shown in FIG. 21, the trend graph begins at a zeta value for air (8.4 $\zeta$) and stabilizes at the value for air fully saturated with PFOB vapor (7.8 $\zeta$).

PFC EVAPORATIVE LOSS

FIG. 22A shows how PFC vapor levels are employed to quantify PFC evaporative loss during partial liquid ventilation. As described in the Background section above, a portion of breathable liquid (e.g., PFC) is lost due to evaporation into the lungs. This evaporated liquid becomes absorbed by the lungs by diffusing into the blood near the lungs and around the alveoli. It eventually leaves the patient's body by transpiration through the skin. A gas collection device 118 is attached to and/or pressed against the skin of an animal or patient 120. The device 118 may be a skin patch or collection vial.

FIG. 22B shows an exploded view of the collection region and a simplified illustration of device 118 against the outer surface of the skin 119. A small gas stream flows through a sampled region associated with the area of the device 118. The gas flow into the region is pure (i.e., unsaturated by PFC). If there is a measurable PFC evaporative loss from the skin, the gas flow out of the region will have a detectable saturation level. This gas flow output of the device 118 is connected directly to thermal conductivity detector/analyzer 10 to detect the saturation level. To quantify the PFC evaporative loss from the sampled region, Equation 7 is employed, wherein $V_R$ is the gas flow from the sampled region.

Knowing the amount of evaporative loss is important because it improves the accuracy of the amount of PFC liquid known to be in the lungs. The amount in the lungs is equal to the amount originally input minus the amount volatilized, minus the amount evaporated. The amount volatilized is calculated from zeta values sampled from the endotracheal tube. The amount evaporated will be functionally related to the zeta value determined from the scheme in FIG. 22A.

To quantify the total PFC evaporative loss from the entire body, the evaporation determined from the sampled region is extrapolated. For example, if the device 118 is a skin patch, the skin patch will cover a known percentage of the skin's total surface area. The evaporation from the surface area of the skin patch will thus be a known percentage of the total evaporation from the entire body. Standard skin surface area values are known for humans of a given age, size, weight and the like.

During partial liquid ventilation, evaporative losses are very small compared to losses from the respiratory system. For example, evaporative losses may be 1/50 of the amount lost from the respiratory system. However, an accurate quantification of the total PFC loss during partial liquid ventilation should preferably include the amount lost from evaporation.

PFC-BLOOD SUBSTITUTE

Emulsions of PFC have been found to be a suitable blood substitute, capable of dissolving oxygen and carbon dioxide. However, when PFC is employed for this purpose, evaporative loss occurs via the skin and the respiratory system (e.g., the lungs). There is a need to quantify this evaporative loss. The level of PFC vapor in the lungs is related to the evaporative loss, and thus indicates when the PFC in the bloodstream must be replenished.

Figure 23:
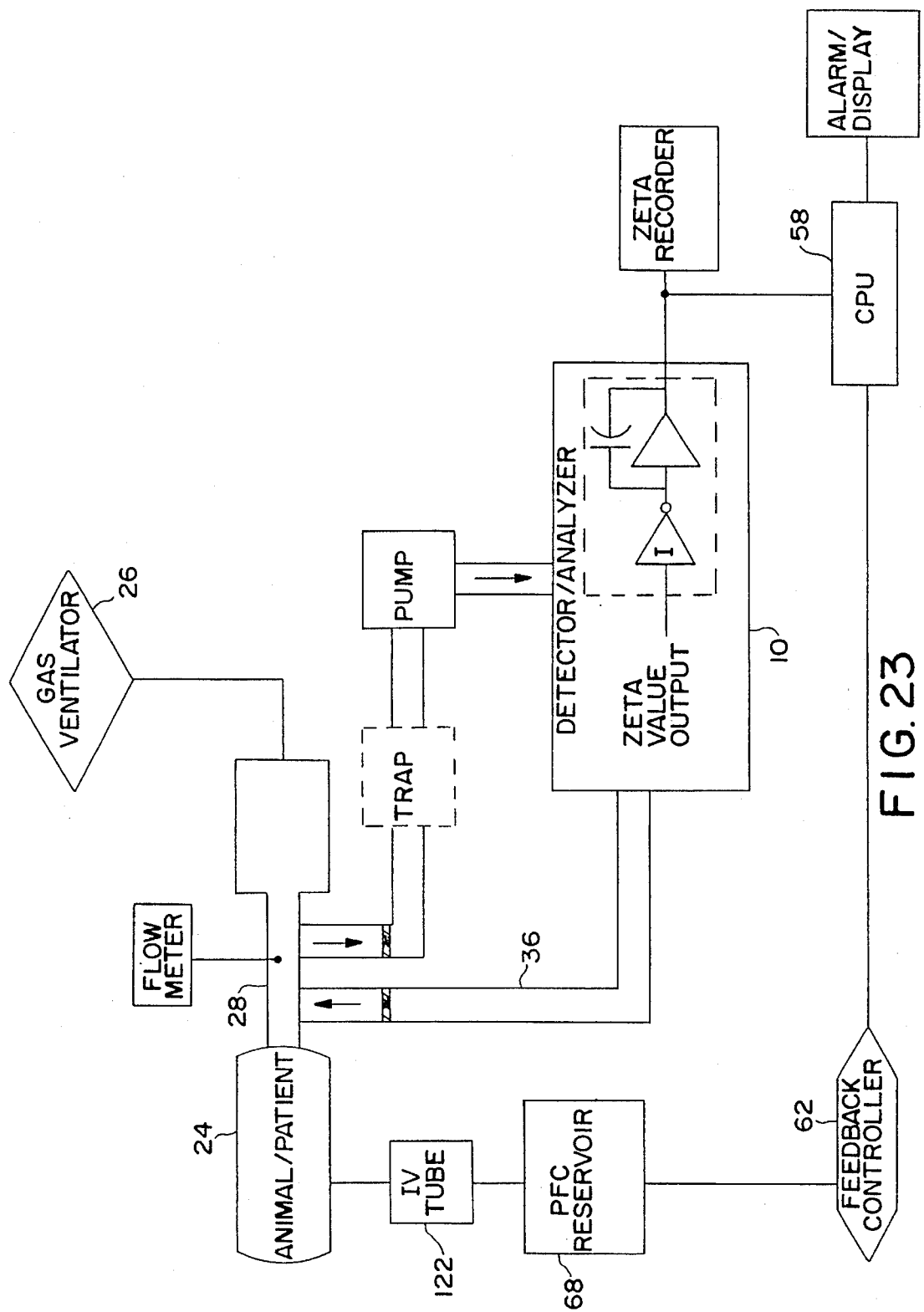
FIG. 23 shows a set-up for monitoring and controlling PFC blood levels after a patient's blood is injected with PFC.

FIG. 23 shows a set-up for monitoring and controlling PFC blood levels after the blood of patient 24 is injected with PFC. Expired respiratory gas containing PFC vapor flows through the endotracheal tube 28, is pumped through the sampling path 36 and is measured by the thermal conductivity detector/analyzer 10. The detector/analyzer 10 outputs a signal to the CPU 58. The CPU 58 is programmed to signal when the PFC vapor in the lungs reaches a preset level and to either alert an operator or automatically add PFC to the patient's bloodstream through feedback controller 62.

The feedback controller 62 causes PFC from the reservoir 68 to flow into intravenous tube 122 connected to the patient's vein. Alteratively, end expiratory sampling of PFC vapor in the lungs can be employed, as shown in FIG. 20, in place of the sampling path 36 and the results fed into the CPU 58 of FIG. 23.

In the set-up shown in FIG. 23, the patient 24 breathes through gas ventilator 26. However, the patient 24 need not be attached to an assisted breathing device. It is only necessary that there be a means, such as, but not limited to, the endotracheal tube 28, a nasal CPAP (continuous positive airway pressure), a mask, or the like, to collect a sample of expired respiratory gas for analysis. Equation 7 is employed to detect PFC loss.

Again, the set-up in FIG. 22A may be employed to detect the amount of transpired PFC during PFC blood substitution. This amount is then added to the amount leaving the patient through the lungs to determine the total amount lost from the bloodstream.

FUNCTIONAL RESIDUAL CAPACITY

The thermal conductivity detector/analyzer 10 can also be employed for correcting conventional Functional Residual Capacity (FRC) patient lung measurements and for measuring FRC in a new way.

FRC is the volume of gas left in the lung (i.e., lung volume) at the end of normal exhalation or expiration. Traditionally, a helium dilution test is employed when making FRC measurements. This test employs thermal detectors. The output of the detectors will be in error if a breathable liquid such as PFC is present in the expired gas. When a patient undergoes partial liquid ventilation, PFC vapor will be present in the expired gas due to volatilization of the PFC liquid. Thus, the FRC measurement will be in error. To correct for this error, the output value of the detector/analyzer 10 is employed to detect the amount of PFC vapor in the lung. This value is then used to offset and normalize the conventionally measured FRC value.

Furthermore, PFC vapor can be employed, instead of helium, as the diluent or tracer gas to make an FRC measurement. Since helium is soluble in blood, large quantities of helium become absorbed during this measurement. PFC vapor is an ideal gas for making such a measurement because it is inert and minimally absorbed into circulation (FRC<<Helium).

To perform this measurement, the patient breathes from a bag of known volume and containing a known quantity of PFC vapor.

The FRC is calculated using the following equation which is a modification or rearrangement of Fick's law:

$$FRC = V_i[(C_i/C_f) - 1] \quad \text{(Equation 9)}$$

where $V_i$ is the system volume (i.e., the volume of the bag), $C_i$ is the initial concentration of PFC vapor in the bag, and $C_f$ is the final concentration of PFC vapor in the bag. System volume, $V_i$, was also determined by rearrangement of Fick's Law. Various known syringe volumes can be accurately assessed in this fashion.

The final concentration of PFC vapor in the bag, $C_f$, is determined by taking a syringe sample and employing the set-up shown in FIG. 20. The resultant zeta value is then correlated to the percent concentration using information from the graph of FIG. 7.

PFC vapor is also suitable for use as a tracer gas for other types of pulmonary function evaluations including the determination of static lung volumes, including residual volume and total lung capacity. PFC vapor is less expensive than current diluent gases currently employed in these tests. PFC vapor may be used in the standard equipment employed for washout and single breath techniques (either closed or open circuit) present in most hospitals. PFC vapor may also be applied in gas mixing analysis for distribution of ventilation in obstructive lung disease.

RADIOLOGIC DIAGNOSIS

Certain breathable liquids such as PFC are radiopaque and make ideal contrast agents for high resolution computed tomography (CT). Thus, a CT scan of the lungs made during partial liquid ventilation provides an image of the PFC in the lungs. The image is used to assess distribution of the PFC in the lungs. However, the scan can be misleading because it does not distinguish between PFC in the alveolar spaces and PFC in the pulmonary interstitium. The thermal conductivity detector/analyzer 10 can be employed in conjunction with CT to alleviate this problem. The level of PFC-gas interaction is assessed either before or after the scan, thus providing correlation with the physician's diagnosis. A high level of interaction indicates a significant quantity of PFC appearing in the CT scan is in the alveolar spaces, whereas a low level of interaction indicates that the PFC is primarily in the pulmonary interstitium.

PFC DELIVERED AGENTS AND THERAPIES

The thermal conductivity detector/analyzer 10 can be employed during pulmonary administration of drugs (PAD). During PAD, the level of PFC vapor in the lungs can be used to estimate bioavailability of the relevant pharmacologic agent or anesthetic. Accurate assessment of PFC-gas interaction and relative amount of PFC in the lungs is also important during intratracheal instillation of PFC for treatment of meconium aspiration syndrome (MAS), congenital diaphragmatic hernia (CDH), neonatal respiratory distress syndrome (NRDS), and other pulmonary pathologies.

FIG. 3 shows one type of thermal conductivity detector suitable the invention. However, other types of thermal conductivity detectors which measure the conductivity of respiratory gases are also within the scope of the invention.

The systems and methods described above employ a thermal conductivity measurement device for ascertaining the PFC-gas interaction. However, other types of analyzers, including a spectrophotometer or a gas chromatograph may be employed in place of the thermal conductivity detector/analyzer 10. These devices are equally able to distinguish between PFC vapor and other types of gases (e.g., air, oxygen) due to differences in electron density. However, they are less cost-effective than the currently described measurement device.

Furthermore, as is well-known in the art, the elements of the thermal conductivity detector/analyzer 10 can be employed to measure other properties of the gas flowing therethrough, including mass or pressure. For example, if the thermistors are employed in a mass flow detector, the zeta value will vary with the mass of the sample. The zeta value would then be precalibrated with gases of known PFC percent saturation amounts in the same manner as the thermal conductivity detector/analyzer described herein. That is, the second y-axis in FIGS. 10, 11, 16 and 17 labelled "Percent saturation with PFC" will be shifted up or down so that it properly correlates with the appropriate zeta values. Thus, the zeta value of the detector/analyzer 10 need not necessarily be the result of a thermal conductivity measurement. The scope of the invention includes any type of measurement detector/analyzer which outputs signal levels (e.g, discrete zeta values) that may be correlated with percent saturation of the gas sample.

When it is desired to determine the quantity of PFC liquid in expired respiratory gas, the flowmeter 56 is employed. Instantaneous flow rate measurements are taken and sent to the CPU 58. The flow rate measurements are correlated with liquid volume amounts associated with a zeta value measurement taken at the same instance. These values, along with the liquid/vapor conversion factor from Equation 7, are then employed to determine the totall amount of lost liquid PFC.

One example of an experimental volume loss calculation is as follows:

Gas Flow into TLV diffuser=8 L/min.

% saturation (zeta)=100%

Temperature=37 degrees Celsius

Time course=30 minutes $$PFC \text{ volume loss} = (8000 \text{ ml/min}) \times [(1.447 \text{ ml PFOB}/100 \text{ ml air}) \times 100\%] \times (1 \text{ ml fluid}/86 \text{ ml vapor}) \times 30 \text{ minutes} = 40.3 \text{ ml}$$

Thus, the PFC volume loss in 30 minutes is 40.3 ml.

The invention disclosed above allow for significantly improved control of liquid ventilation processes. No longer does an operator have to guess if, and how much, PFC must be added to a patient's lungs to optimize PFC-gas interaction and to replace volatilized and evaporated PFC liquid. The invention also describes simple and cost-effective techniques to add a PFC recovery to total liquid ventilation systems and to maximize the efficiency of the recovery system. Furthermore, the invention describes how PFC saturation values are useful in a wide variety of other biomedical applications.

The present invention may be embodied in other specific forms without departing from the spirit or essential attributes thereof and, accordingly, reference should be made to the appended claims, rather than to the foregoing specification, as indicating the scope of the invention.

We claim:

1. A process for determining the amount of interaction in a mammalian lung between a breathable liquid in the lung and a respiratory gas flowing into and out of a pulmonary pathway in communication with the lung, said process comprising the steps of:
   (a) sampling expired respiratory gas from the pulmonary pathway;
   (b) passing the sampled gas through a measurement detector, the detector outputting a discrete value representative of a property of the gas;
   (c) comparing the discrete value to previously determined discrete values representative of respiratory gas fully saturated with vapors of breathable liquid and respiratory gas unsaturated by vapors of breathable liquid; and
   (d) determining from the comparison the amount of interaction, wherein discrete values near the fully saturated discrete value indicates maximum interaction and discrete values near the unsaturated discrete value indicates minimum interaction.

2. A process in accordance with claim 1 wherein the sampling of the expired respiratory gas comprises sampling said gas from an endotracheal tube connected at one end to the pulmonary pathway and at the other end to a gas ventilator.

3. A process in accordance with claim 2 comprising returning the sampled gas to the endotracheal tube after sampling.

4. A process in accordance with claim 2 comprising pumping the sampled gas through a closed loop sampling path which includes the measurement detector.

5. A process in accordance with claim 1 wherein the breathable liquid is perfluorocarbon.

6. A process in accordance with claim 1 wherein the measurement detector is a thermal conductivity detector and the discrete value is representative of the thermal conductivity of the gas.

7. A process for determining the volume loss rate of breathable liquid in a lung while respiratory gas flows into and out of a pulmonary pathway in communication with the lung, said process comprising the steps of:
   (a) measuring the minute ventilation, $V_M$;
   (b) sampling expired respiratory gas from the pulmonary pathway;
   (c) passing the sampled gas through a measurement detector, the detector outputting a discrete value representative of a property of the gas;
   (d) correlating the output discrete value of the measurement detector to a percentage by volume of breathable liquid vapor in the gas; and
   (e) calculating the volume loss rate of expired breathable liquid from the equation:

$$V_M \times (\% \text{ by volume of breathable liquid vapor in the gas}) \times C_{LV},$$

where $C_{LV}$ is a liquid/vapor conversion factor for the breathable liquid.

8. A process in accordance with claim 7 wherein the breathable liquid is perfluorocarbon.

9. A process in accordance with claim 7 wherein the measurement detector is a thermal conductivity detector and the discrete value is representative of the thermal conductivity of the gas.

10. A process for controlling the amount of breathable liquid in a lung while respiratory gas flows into and out of a pulmonary pathway in communication with the lung, said process comprising the steps of:
    (a) measuring the minute ventilation, $V_M$;
    (b) sampling expired respiratory gas from the pulmonary pathway;
    (c) passing the sampled gas through a measurement detector, the detector outputting a discrete value representative of a property of the gas;
    (d) correlating the output discrete value of the measurement detector to a percentage by volume of breathable liquid vapor in the gas;
    (e) calculating the volume loss of expired breathable liquid from the equation:

$$V_M \times (\% \text{ by volume of breathable liquid vapor in the gas}) \times \text{total ventilation time} \times C_{LV},$$

where $C_{LV}$ is a liquid/vapor conversion factor for the breathable liquid; and (f) adding breathable liquid to the lung from a reservoir of breathable liquid in fluid communication with the lung to replenish the lost volume.

11. A process in accordance with claim 10 wherein the breathable liquid is perfluorocarbon.

12. A process in accordance with claim 10 wherein the measurement detector is a thermal conductivity detector and the discrete value is representative of the thermal conductivity of the gas.

13. A process for determining and controlling the amount of interaction in a mammalian lung between a breathable liquid in the lung and a respiratory gas flowing into and out of a pulmonary pathway in communication with the lung, said process comprising the steps of:

(a) sampling expired respiratory gas from the pulmonary pathway;

(b) passing the sampled gas through a measurement detector, the detector outputting a discrete value representative of a property of the gas;

(c) comparing the discrete value to a range of previously determined discrete values, one end of the range representing respiratory gas fully saturated with vapors of breathable liquid and the other end of the range representing respiratory gas unsaturated by vapors of breathable liquid;

(d) determining from the comparison the amount of interaction, wherein discrete values near the fully saturated discrete value indicates maximum interaction and discrete values near the unsaturated discrete value indicates minimum interaction; and (e) performing at least one intervening function to increase the amount of interaction if it decreases below a preset amount.

14. A process in accordance with claim 13 wherein the intervening function includes repositioning the mammal, thereby repositioning the lung.

15. A process in accordance with claim 14 wherein the mammal is positioned on a platform and the repositioning includes the step of reorienting the platform.

16. A process in accordance with claim 14 wherein a reservoir of breathable liquid is in fluid communication with the lung, and a second intervening function includes adding breathable liquid from the reservoir to the lung if the repositioning fails to increase the amount of interaction to the preset amount.

17. A process in accordance with claim 13 wherein a reservoir of breathable liquid is in fluid communication with the lung, and the intervening function includes adding breathable liquid in the reservoir to the lung.

18. A process in accordance with claim 13 wherein the measurement detector is a thermal conductivity detector and the discrete value is representative of the thermal conductivity of the gas.

19. A process for monitoring and reducing residual amounts of breathable liquid in a mammalian lung after switching from ventilating the lung with breathable liquid to ventilating the lung with gas, respiratory gas flowing into and out of a pulmonary pathway in communication with the lung, said process comprising the steps of:

(a) sampling expired respiratory gas from the pulmonary pathway;

(b) passing the sampled gas through a measurement detector, the detector outputting a discrete value representative of a property of the gas;

(c) comparing the discrete value to a range of previously determined discrete values, one end of the range representing respiratory gas fully saturated with vapors of breathable liquid and the other end of the range representing respiratory gas unsaturated by vapors of breathable liquid;

(d) determining from the comparison the amount of interaction, wherein discrete values near the fully saturated discrete value indicates maximum interaction between the residual breathable liquid in the lung and the respiratory gas flowing into and out of the lung and discrete values near the unsaturated discrete value indicates minimum interaction therebetween;

(e) calculating the rate of change of the amount of interaction; and (f) performing at least one intervening function to increase the amount of interaction, and thereby more quickly deplete the residual amount of breathable liquid, if the rate of change is below a preset amount.

20. A process in accordance with claim 19 wherein the pulmonary pathway is connected to a gas ventilator and the intervening function includes increasing the respiratory rate of the ventilator.

21. A process in accordance with claim 19 wherein the pulmonary pathway is connected to a gas ventilator and the intervening function includes increasing the inspiratory pressure of the ventilator.

22. A process in accordance with claim 19 wherein the measurement detector is a thermal conductivity detector and the discrete value is representative of the thermal conductivity of the gas.

23. A process for monitoring the operation of a breathable liquid vapor recovery system which recovers breathable liquid from a stream of gas input thereto, the process comprising the steps of:

(a) sampling gas at an output of the recovery system;

(b) passing the sampled gas through a measurement detector, the detector outputting a discrete value representative of a property of the gas; and (c) comparing the measured discrete value to a desired preset discrete value indicating proper operation of the recovery system, the desired preset discrete value being within a range of previously determined discrete values, one end of the range representing respiratory gas fully saturated with vapors of breathable liquid and the other end of the range representing respiratory gas unsaturated by vapors of breathable liquid.

24. A process in accordance with claim 23 wherein the measurement detector is a thermal conductivity detector and the discrete value is representative of the thermal conductivity of the gas.

25. A process for monitoring and controlling the operation of a breathable liquid vapor recovery system which recovers breathable liquid from a stream of gas input thereto, the system including a condenser for condensing the vapors of the breathable liquid and a thermostat for controlling the temperature of the condenser, the process comprising the steps of:

(a) sampling gas at an output of the recovery system;

(b) passing the sampled gas through a measurement detector, the detector outputting a discrete value representative of a property of the gas;

(c) comparing the measured discrete value to a desired preset discrete value indicating proper operation of the recovery system, the desired preset discrete value being within a range of previously determined discrete values, one end of the range representing respiratory gas fully saturated with vapors of breathable liquid and the other end of the range representing respiratory gas unsaturated by vapors of breathable liquid; and (d) adjusting the set point of the condenser thermostat in response to a measured discrete value which is significantly different than the desired preset value.

26. A process in accordance with claim 25 wherein the recovery system receives the stream of gas from a carbon dioxide removal system having an oxygenator/diffuser and a pump, the process further including the step of (e) adjusting the flow rate of the pump in response to a measured discrete value which is significantly different than the desired preset value.

27. A process in accordance with claim 25 wherein the measurement detector is a thermal conductivity detector and the discrete value is representative of the thermal conductivity of the gas.

28. A process for quantifying the evaporative loss rate of liquid perfluorocarbon from the blood supply of a mammal via the respiratory system when the perfluorocarbon is employed as a blood substitute, the process comprising the steps of:

(a) injecting perfluorocarbon into the bloodstream of a mammal;

(b) measuring the minute ventilation, $V_M$;

(c) sampling expired respiratory gas from a pulmonary pathway of said mammal;

(d) passing the sampled gas through a measurement detector, the detector outputting a discrete value representative of a property of the gas;

(e) correlating the output discrete value of the measurement detector to a percentage by volume of perfluorocarbon vapor in the gas;

(f) calculating the volume loss rate of expired perfluorocarbon liquid from the equation:

$$V_M \times (\% \text{ by volume of breathable liquid vapor in the gas}) \times C_{LV},$$

where $C_{LV}$ is a liquid/vapor conversion factor for the perfluorocarbon liquid, the volume loss rate of expired perfluorocarbon representing the evaporative loss rate via the respiratory system.

29. A process in accordance with claim 28 wherein the measurement detector is a thermal conductivity detector and the discrete value is representative of the thermal conductivity of the gas.

30. A process for quantifying the evaporative loss of liquid perfluorocarbon from a mammal via transpiration loss through the skin, the process comprising the steps of:

(a) placing a collection device against an area of the mammal's skin and collecting a sample of gas therefrom;

(b) passing the sampled gas through a measurement detector, the detector outputting a discrete value representative of a property of the gas, the discrete value having a range which at one end represents respiratory gas fully saturated with vapors of perfluorocarbon and at the other end represents respiratory gas unsaturated by vapors of perfluorocarbon; and (c) correlating the output discrete value of the measurement detector to a discrete value indicative of the total transpiration loss.

31. A process in accordance with claim 30 wherein the measurement detector is a thermal conductivity detector and the discrete value is representative of the thermal conductivity of the gas.

32. A process employing perfluorocarbon vapor to determine the functional residual capacity, FRC, of a mammal's lung, the process comprising the steps of:

(a) breathing from a container of known volume, $V_i$, and containing a known concentration, $C_i$, of perfluorocarbon vapor for a predetermined period of time;

(b) sampling the gas in the container after the predetermined period of time;

(c) passing the sampled gas through a measurement detector, the detector outputting a discrete value representative of a property of the gas, the discrete value having a range which at one end represents respiratory gas fully saturated with vapors of perfluorocarbon and at the other end represents respiratory gas unsaturated by vapors of perfluorocarbon;

(d) correlating the output discrete value of the measurement detector to a final concentration, $C_f$, of perfluorocarbon vapor in the container; and (f) determining the functional residual capacity by the formula $$FRC = V_i[(C_i/C_f) - 1].$$

33. A process in accordance with claim 32 wherein the measurement detector is a thermal conductivity detector and the discrete value is representative of the thermal conductivity of the gas.

34. A method for correcting errors in a functional residual capacity measurement made while a patient undergoes partial liquid ventilation with a breathable liquid, the errors being caused by the presence of vapors of the breathable liquid in expired respiratory gas, the method comprising the steps of:

(a) measuring the functional residual capacity of a patient;

(b) sampling expired respiratory gas from the patient's pulmonary pathway, the pathway being in communication with the lung;

(c) passing the sampled gas through a measurement detector, the detector outputting a discrete value representative of a property of the gas, the discrete value having a range which at one end represents respiratory gas fully saturated with vapors of the breathable liquid and at the other end represents respiratory gas unsaturated by vapors of the breathable liquid;

(d) calculating from said discrete value the amount of breathable liquid vapor in the sampled gas; and (e) adjusting the functional residual capacity measurement by said amount of breathable liquid vapor.

35. A process in accordance with claim 34 wherein the measurement detector is a thermal conductivity detector and the discrete value is representative of the thermal conductivity of the gas.

* * * * *